United States Patent [19]
Jackson

[11] Patent Number: 5,591,165
[45] Date of Patent: Jan. 7, 1997

[54] APPARATUS AND METHOD FOR SPINAL FIXATION AND CORRECTION OF SPINAL DEFORMITIES

[75] Inventor: Roger P. Jackson, Prairie Village, Kans.

[73] Assignee: Sofamor, S.N.C., Rang-Du-Fliers, France

[21] Appl. No.: 244,435

[22] PCT Filed: Oct. 15, 1993

[86] PCT No.: PCT/US93/09919

§ 371 Date: May 25, 1994

§ 102(e) Date: May 25, 1994

[87] PCT Pub. No.: WO94/10944

PCT Pub. Date: May 26, 1994

[30] Foreign Application Priority Data

Nov. 9, 1992 [FR] France .................................. 92 13476

[51] Int. Cl.$^6$ ...................................................... A61B 17/70
[52] U.S. Cl. .................................. 606/61; 606/72; 606/60
[58] Field of Search ................................ 606/61, 60, 59, 606/54, 72, 73, 76, 90, 101, 105; 623/17

[56] References Cited

U.S. PATENT DOCUMENTS

| 4,887,596 | 12/1989 | Sherman | 606/61 |
|---|---|---|---|
| 4,987,892 | 1/1991 | Krag et al. | 606/61 |
| 5,002,542 | 3/1991 | Frigg | 606/61 |
| 5,067,955 | 11/1991 | Cotrel | 606/61 |
| 5,127,912 | 7/1992 | Ray et al. | 606/61 |
| 5,129,388 | 7/1992 | Vignaud et al. | 606/61 |
| 5,129,900 | 7/1992 | Asher et al. | 606/61 |
| 5,176,680 | 1/1993 | Vignaud et al. | 606/61 |
| 5,254,118 | 10/1993 | Mirkovic | 606/61 |
| 5,385,583 | 1/1995 | Cotrel | 623/17 |
| 5,389,099 | 2/1995 | Hartmeister et al. | 606/61 |

FOREIGN PATENT DOCUMENTS

| 0348272 | 12/1989 | European Pat. Off. . | |
| 9311715 | 6/1993 | WIPO | 606/61 |

Primary Examiner—Guy V. Tucker
Attorney, Agent, or Firm—Woodard, Emhardt, Naughton, Moriarty & McNett

[57] ABSTRACT

This device comprises an connection element (4) between a rod (1), or other longitudinal implant, and a bone anchorage screw (3) in the degenerative vertebra. This connection element (4) includes a ring (8) so dimensioned that the rod (1) is capable of extending therethrough. The ring is provided with screws (14) for clamping to the rod (1) and is radially extended by a cylindrical arm (9) adapted to be secured to the bone anchorage screw (3) and to be clamped on the screw. The arm (9) and the ring (8) constitute a unit in one piece. The invention enables the surgeon to avoid having to produce additional deformations of the rod (1) when it is in presence of non-aligned pedicles by leaving to the surgeon complete liberty as to the position of the two axes of the bone anchorage screw (3) and of the rod (1). The invention further contemplates using the lateral connection element to facilitate contouring the longitudinal implant within the patient, or in situ to segmentally and globally correct spinal deformities in all degrees of freedom.

26 Claims, 13 Drawing Sheets

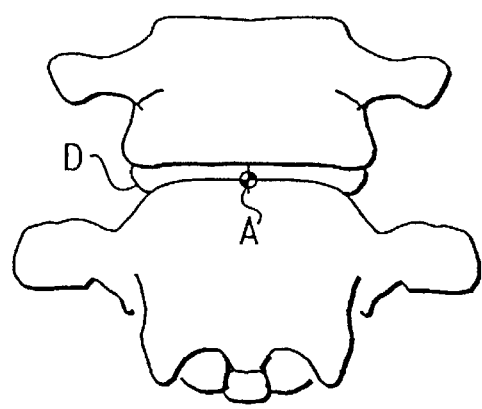
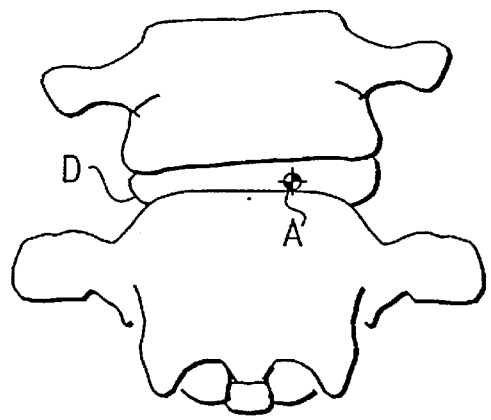
Fig. 7A  Fig. 7B
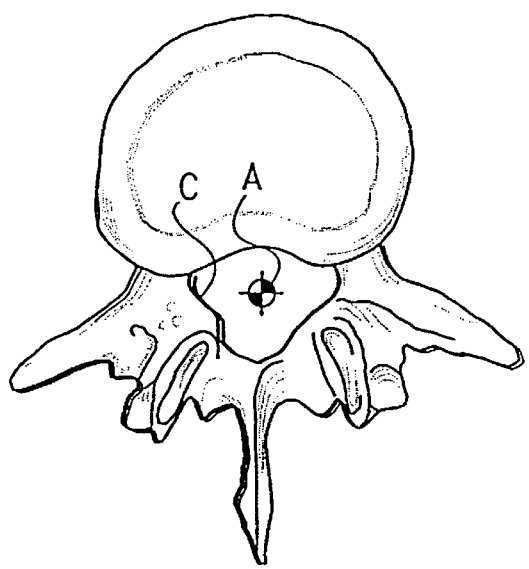
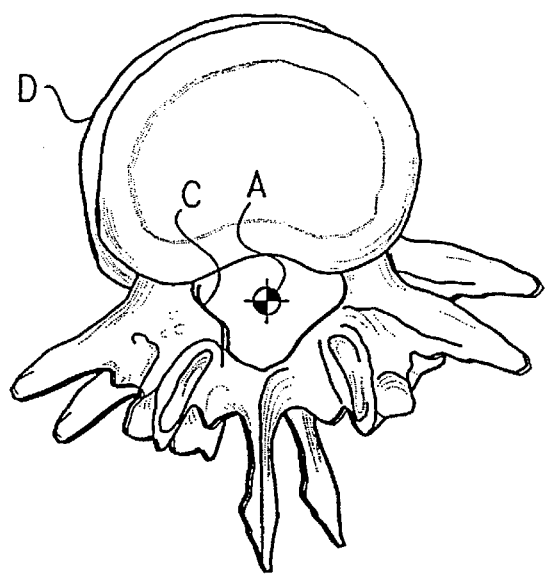
Fig. 8A  Fig. 8B

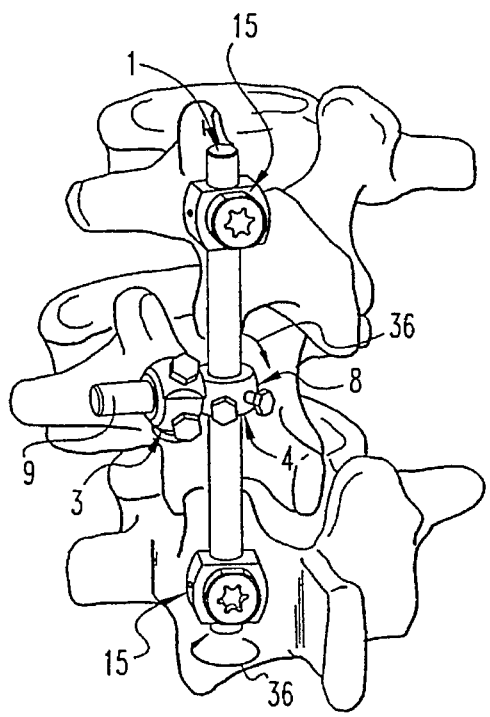
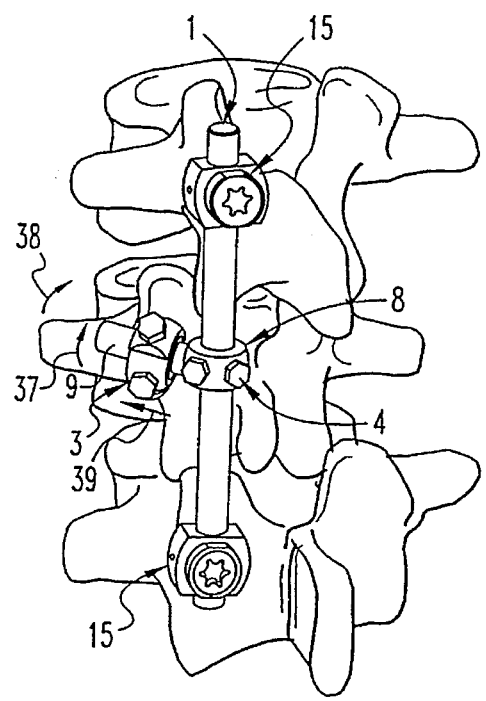
*Fig. 11A*  *Fig. 11B*
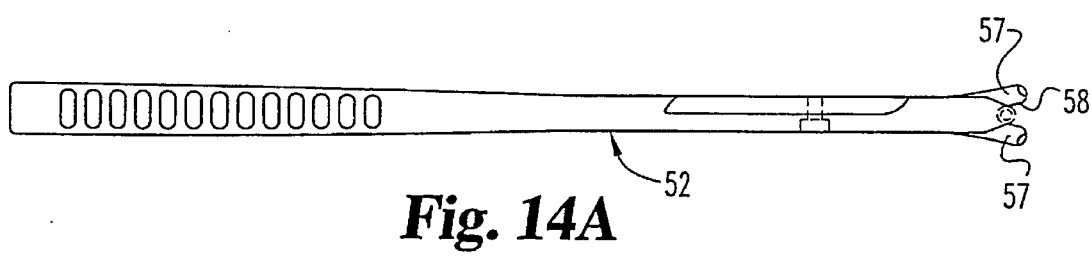
*Fig. 14A*
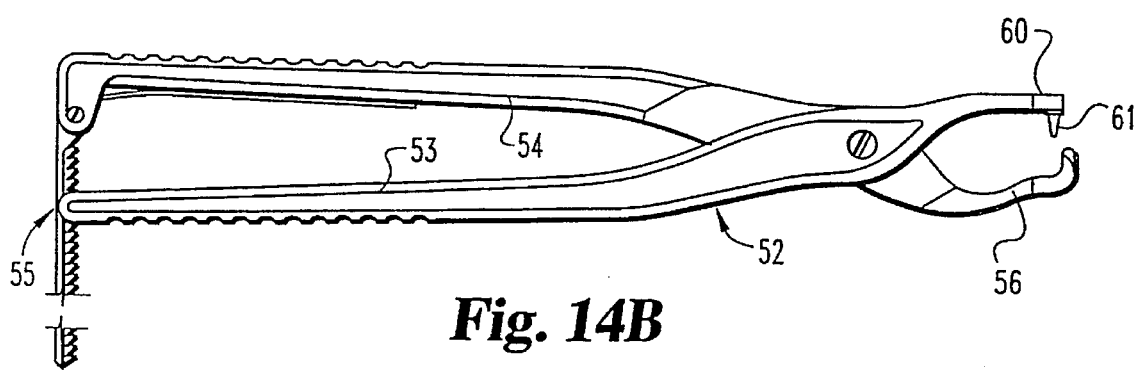
*Fig. 14B*

BEFORE

AFTER

BEFORE

AFTER

BEFORE

APPARATUS AND METHOD FOR SPINAL FIXATION AND CORRECTION OF SPINAL DEFORMITIES

This application is a 35 U.S.C. 371 application of PCT/ US95/09919, filed Oct. 15, 1993.

BACKGROUND OF THE INVENTION

The present invention concerns an apparatus for spinal osteosynthesis, applicable notably to degenerative or misaligned vertebrae.

It is known that the vertebrae, in particular the lumbar vertebrae, are subjected to a concentration of stresses, in which the discs and the ligaments play a significant compensating part. If these vertebrae belong to a relatively aged body, they undergo a certain degeneration, which makes the discs and the ligaments unable to completely fulfill their role by reason of their aging.

These vertebrae then, are subjected to a certain instability and tend to displace relative to adjacent vertebrae. These displacements are uncontrolled and can be: displacements in angularion and rotation, medio-lateral and antero-posterior displacements, or else the combination of these displacements.

It is therefore necessary to remedy this situation, which risks generating a compression or compromise of the spinal cord of the patient, by endeavoring to put the displaced or misaligned vertebrae back to their positions.

SUMMARY OF THE INVENTION

The spinal osteosynthesis device, according to the invention, comprises at least one longitudinal implant, such as a rod, and by preference two, together with bone anchorage elements joined to the rod, such as screws or hooks.

In accordance with the invention, this device comprises at least one connection element between the rod and a vertebra to be treated, and means for fixation of this element to the vertebra, this element including a body, such as a ring or collar, so dimensioned that the rod can be mounted therein to move freely in rotation and in translation on the rod and outfitted with means for fixing the ring on the rod and extended radially by an arm, this arm and the ring forming a one-piece unit.

In this way the terminal ring of the connection element can be mounted to be trapped on the osteosynthesis rod or longitudinal implant, while being still free in translation and in rotation before its fixation in the chosen position on the osteosynthesis rod, by way of a suitable means for fixing.

According to one aspect of the invention, the means for fixation of the connection element to the vertebra to be treated is advantageously a bone anchorage element, such as a screw or a hook of a known type, and whose body is open in a U-shape in order to permit introduction into it of the free end of the arm of the connection element. The invention contemplates that the anchorage element be free to both translate medio-laterally along and rotate/angulate around the extended radial arm of the connection element. This aspect of the invention can be implemented with a hook having a closed body with the longitudinal implant or rod extending through an opening in the hook body.

In another aspect of the invention, the aforementioned lateral connection element is used in a novel method for correction of a spinal deformity. This method provides for correction segmentally along the entire length of the spine, in all three degrees of freedom and along the three columns (posterior, middle and anterior) of the spine. This method contemplates implanting a strong yet ductile longitudinal implant between several vertebrae. In one embodiment, the implant is an osteosynthesis rod, although this method can be applied using a bar or plate. The vertebrae are instrumented with fixation elements, such as hooks or screws, and the fixation elements are engaged to the longitudinal implant, or rod, in a manner that permits free sliding translation and rotation of the fixation elements with respect to the rod. In the preferred embodiments, this engagement is effected by the lateral connection element.

Once the instrumentation is in position, the spinal rod is contoured within the patient, or in situ, until the rod has assumed the shape of a properly oriented spine. As the rod is contoured in situ, the fixation elements engaged to the vertebrae impart corrective forces to the successive motion segments. Since the fixation elements are free to translate and rotate relative to the rod-being contoured, the motion segments are allowed to automatically and naturally seek their proper anatomic position. This in situ contouring approach involves manipulation of the motion segments so that the axes of movement of the segments is as near to the neuroforamina as possible to avoid the risk of compromising the neural canal.

An important feature of the invention that permits application of the in situ contouring approach is the material properties of the longitudinal implant. The implant must naturally be strong enough to withstand the often severe loads imposed on it by the spine. The implant must also be stiff enough to resist deformation under these loads once the instrumentation is complete. At the same time, the implant must be formed of a material that is sufficiently ductile to allow the implant to be deformed within the patient and substantially retain that imposed deformation. Given the narrow confines in the spinal region, it is undesirable to "over contour" the implant with the expectation that the "springback" properties of the implant will decrease the final deformation. Thus, the implant material preferably exhibits an optimum ductility, or more particularly, maintains in its final position a high percentage of the imposed deformation.

In order to achieve this novel in situ contouring and correction, specially designed tools are provided. One tool, a traction rotator, is configured to engage the ends of a lateral connection element so as to provide a rotational force to the element. In addition, the traction rotator can have forked arms at its end to contact a body engaged to the arm of the lateral connection element to apply a traction force to that body. A second tool, a counter-rotator, is configured to engage the lateral connection element at a lower vertebral level to hold this lower element fixed while a subsequent level is operated on by the traction rotator.

Bending irons are set forth in a further aspect of the invention which are specially suited for manifesting this in situ contouring approach. A right angle or L-bender permits bending the rod within the patient in the sagittal plane. A rod grip bender provides a cylindrical surface for gripping the rod as it is bent. This rod grip bender greatly reduces the local deformation experienced by the rod as the bending force is transmitted through the bender to the rod.

The present invention contemplates instrumentation over several lumbar arid thoracic vertebral levels. In addition, another feature of the invention resides in intrasacral fixation at the distal end of the longitudinal implant. In accordance with one embodiment, the longitudinal implant, such as a rod, is extended into a bore formed inferiorly from the L5-S1 junction. A sacral screw having an oblique canal for receiving the rod is buried into the lateral sacral mass, generally beneath the iliac crest. The iliac crest provides a "buttressing" effect to resist pullout of the sacral screw and to help alleviate the loads exerted on the screw and rod at the L5-S1 junction by pelvic rotation and bending. This "iliac buttress" combines with the proximal sacral screw and the distal rod engagement within the sacrum to form a firm and strong foundation for the longitudinal spinal instrumentation.

In yet another aspect of the invention, the lateral connection element can be used to position a plurality of vertebral fixation elements at a single level. In one embodiment, one lateral connection element is engaged to a spinal rod, while another lateral connection element is engaged to the first. On vertebral fixation element is engaged to the rod, while a second fixation element is engaged to the second lateral connection element, which can extend substantially parallel to the principal rod. In this manner, the first and second fixation elements can be oriented laterally virtually side-by-side. For example, a pedicle hook and a supralaminar hook can be situated at the same level. In another embodiment, a laminar hook can be associated with a vertebral fixation screw, so that the hook can strengthen the construct against screw pullout.

It is one object of the present invention to provide a spinal fixation system for the correction of spinal deformities that accommodates multiple, and even variable, positions of a vertebral fixation element relative to a longitudinal implant. Another object resides in a method for correcting the spinal deformity that can be implemented with fixation elements engaged at any one of many positions in the vertebrae.

Some other details and benefits of the inventions will appear in the course of the description which follows, taken in reference to the annexed drawings which illustrate one preferred embodiment by virtue of non-limiting examples.

DESCRIPTION OF THE FIGURES

FIGS. 7A–B are schematic representations of a motion segment viewed posteriorly in the frontal plane and showing the location of the axis of the segment as the spine moves.

FIGS. 8A–B are schematic representations of a motion segment viewed inferiorly in the transverse plane and showing the location of the axis of the segment as the spine moves.

FIGS. 11A–B are perspective views of a spinal segment in which one vertebra is displaced and then subsequently manipulated into its proper anatomic position.

FIGS. 14A–B are top and side elevational views of a traction rotator tool for use in direct derotation of spinal instrumentation in accordance with the present invention.

DESCRIPTION OF THE PREFERRED EMBODIMENTS

Figure 1:
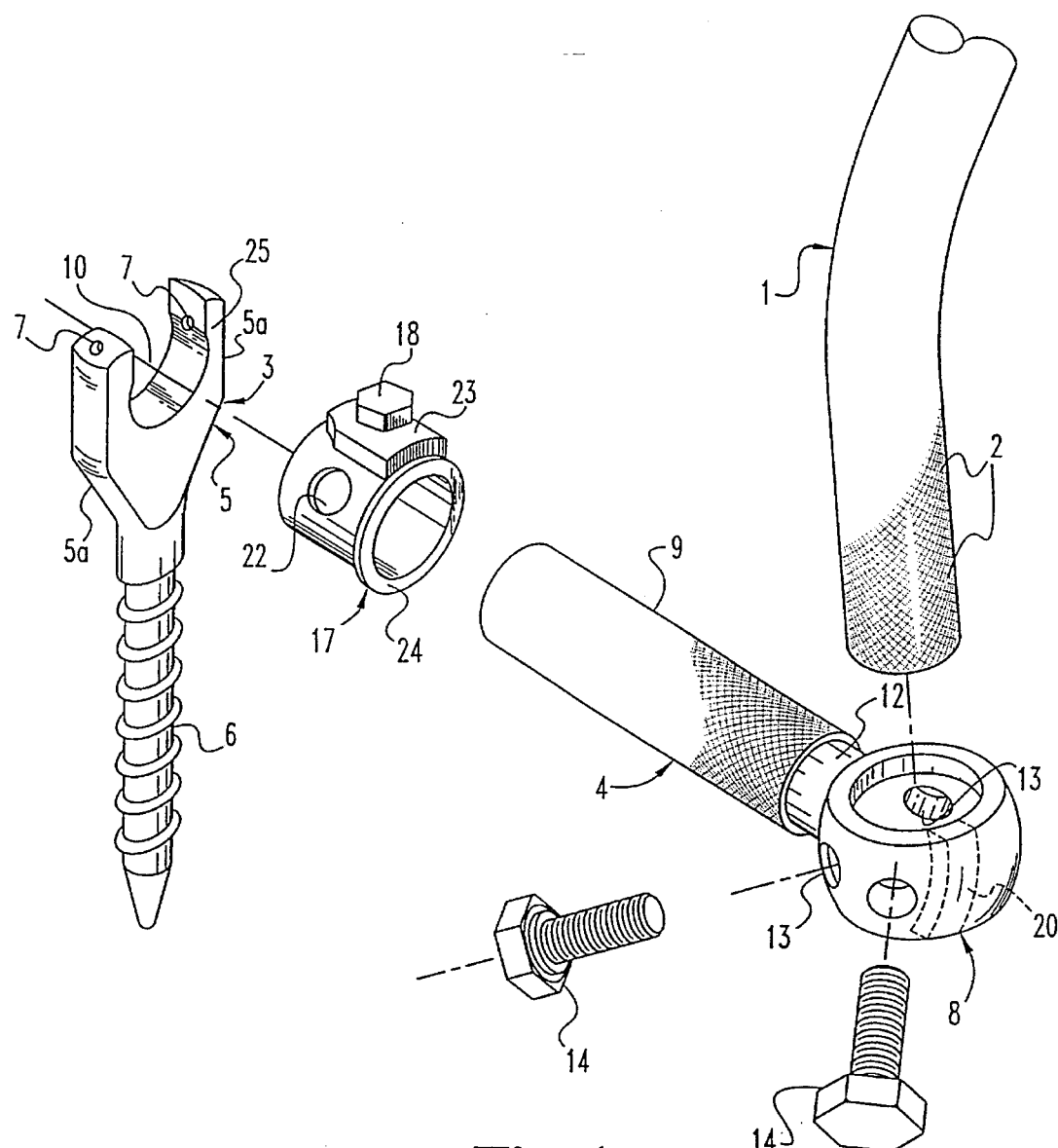
FIG. 1 is a view in exploded partial perspective of one preferred embodiment of a spinal ostheosynthesis device including connection element according to the invention used between an osteosynthesis rod and a bone anchorage screw.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 2:
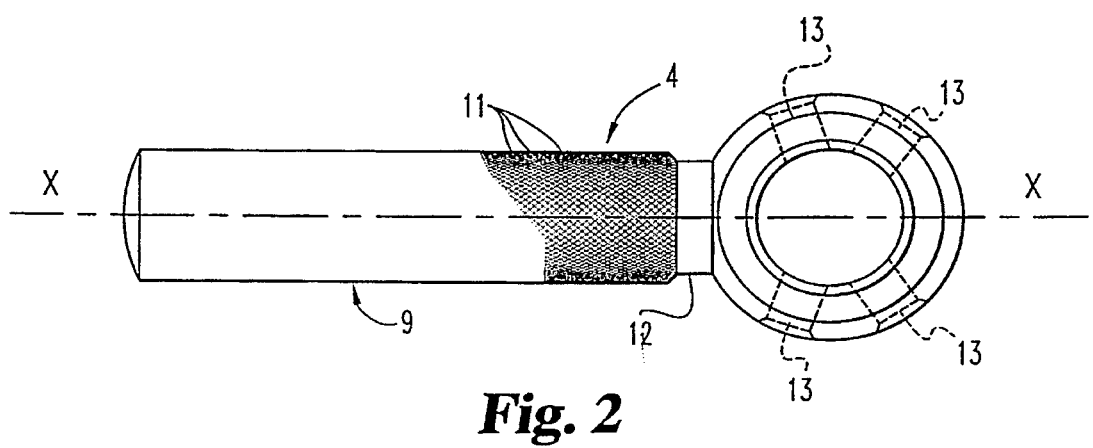
FIG. 2 is a view from above in enlarged scale of the connection element depicted in the FIG. 1.

One sees in FIGS. 1 and 2 an osteosynthesis rod 1 of which the surface presents a multiplicity of asperities 2, for example forming the points of a diamond, a bone anchorage pedicle screw 3 and a connection element 4 between the rod 1 and the screw 3 positioned laterally or medially to the rod 1 in a pedicle.

The pedicle screw 3 is constituted by an open and U-shaped body 5 and by a threaded section 6, which is of the type of the one described in the French patent 89 04 925 (2 45 732) in the name of Yves Cotrel. The screw is normally adapted to receive, between the branches 5a of body 5, a rod 1 with asperities. Threaded apertures 7 are defined in the branches 5a to receive screws 19 (FIGS. 4–5) provided for fixing on the rod, this fixation being completed by a cylindrical clamping member 17 closing channel 10 of body 5.

Clamping member 17 is so dimensioned to be introduced in the U-shaped body 5 with arm 9 extending therethrough. It includes a central screw 18 capable of being screwed into a threaded aperture in a radial boss 23 dimensioned to slide between the ends of the branches 5a. Clamping member 17 is moreover pierced by apertures 22 for passage of the lateral screws 19, and is provided with a collar 24 forming a shoulder adapted for support on a corresponding face 25 defined on an entrance edge of channel 10 of body 5.

The element 4 includes a body, such as ring 8, dimensioned to be able to receive principal rod 1 extended therethrough, and an arm 9, preferably cylindrical and of a diameter substantially equal to the one of the channel 10, extending radially from ring 8 to a suitable length, and forming a one-piece unit with the ring. The arm 9 is adapted to be able to penetrate and Slide in cylindrical channel 10. Its surface preferably presents a multiplicity of asperities 11 (FIG. 2), Which could be similar to asperities 2 on rod 1. The surface of the arm with asperities 11 is joined to ring 8 by a smooth section 12 of diameter slightly smaller than the one of the portion with asperities.

Apertures 13, numbering four in the represented example (although other numbers are possible), are radially disposed in ring 8, so that one pair of apertures is symmetrical to the other pair with respect to diameter XX of ring 8, which intersects the axis of arm 9. These apertures 13 can receive corresponding screws 14 for clamping the element 4 against translation and rotation on rod 1 in the chosen position. The solidity of this fixation is increased by asperities 2 which afford a connection of very high mechanical quality.

Pedicle screw 3 constitutes a means of fixation of arm 9 of element 4 in the degenerative vertebra to be treated. In order to do this, arm 9 is introduced in U-shaped body 5 and blocked by the aforementioned means 7, 17, 18 and 19. Clamping member 17 closes the aperture of the U in body 5 assuring the security of the mounting. Indeed, in the event of the breakage of lateral screw 19, arm 9 cannot, due to the fixing of member 17, become detached from the body 5 of the screw 3.

The ring 8 can be mounted free in translation and in rotation on the principal rod 1 and can then be locked on the rod by the radial means constituted by screws 14.

Alternatively, the means for fixation of arm 9 on the vertebra to be treated can be formed by a threaded plug, according with the teaching of the French patent 2,633,177 (88 08538) or by a system similar to that disclosed in the French patent 2,545,350 (83 07450). The asperities on arm the 9 and on the rod 1 are preferably formed, but not necessarily, according to the French patent 2,545,350 (83.07450). (These asperities constitute the means for anchorage of the extremities of screws 14, 18 and 19.)

Figure 5:
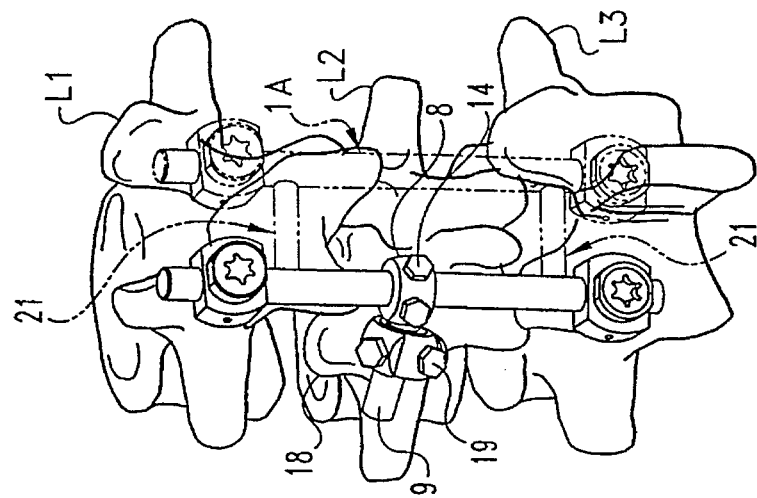
FIG. 5 is an analogous view of FIG. 4 showing the vertebra and the associated pedicle screw in their definitive position, at the end of sliding on the arm of the connection element and after rotation of the ring on the principal rod.
Figure 4:
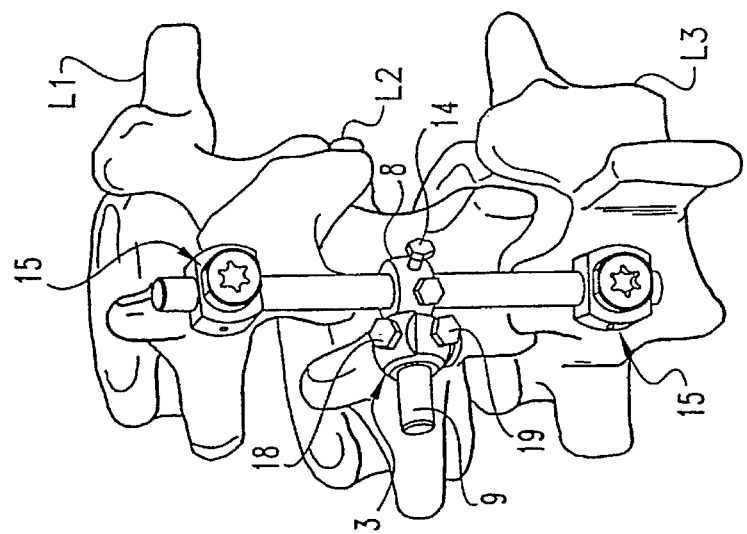
FIG. 4 is an analogous view to FIG. 3 showing a bone anchorage screw and the corresponding vertebra in the course of translation on the arm of the connection element according to the invention.
Figure 3:
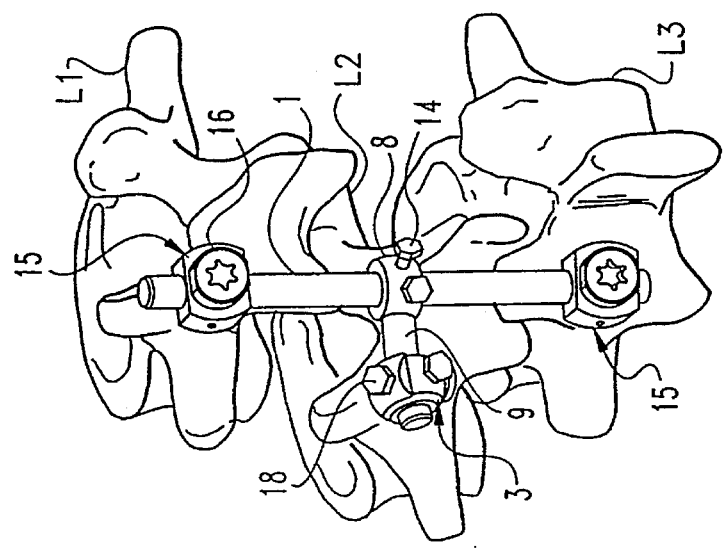
FIG. 3 is a view in perspective of a spinal osteosynthesis instrumentation embodying one device according to the invention, set in position on a spinal section in which one of the vertebrae is displaced to be returned into alignment with the others.

The osteosynthesis instrumentation illustrated in FIGS. 3 to 5 includes two straight rods 1, 1A extending the length of three vertebrae, for example L3, L2, L1, and joined by known transverse connection devices 21. (These devices 21 and the rod 1A are represented in phantom in FIG. 5.) The intermediate vertebra L2 is shifted with relationship to the others and must therefore be restored to its desired position by positioning the instrumentation.

The osteosynthesis device according to the invention is placed in position by the surgeon in the following manner.

The osteosynthesis rods 1 and 1A are firmly set in two points of anchorage to vertebrae adjacent lumbar vertebra L2. The two anchorage points of rod 1 are then accomplished on the adjacent vertebrae L1 and L3, by screws such as 15 (FIG. 3), of a known type. The surgeon completes the mounting with the transverse connection devices 21 jointing rods 1 and 1A (FIG. 5).

The rod is intended to serve as the support for lateral connection element 4, which is previously loosely joined to it by axial introduction of ring 8 on rod 1. The ring 8 becomes trapped but is free in rotation and in translation, in the free space separating fixation screws 15 from osteosynthesis rod 1.

The means for fixation of element 4 to the degenerative vertebra L2 to be treated, for example a pedicle screw 3, is fixed to this vertebra L2. The free end of arm 9 can then be easily introduced in channel 10 of U-shaped body 5, and can stay free in translation and rotation. The action of the surgeon consists then, with the assistance of suitable tools, to reposition the vertebra L2 with relationship to the adjacent vertebrae L1 and L3, to its original position. To do this, the surgeon manipulates body 5 of the screw 3. This having been done, the rotational position of ring 8 in relationship to osteosynthesis rod 1 is automatically modified, and in this way too the position of body 5 of the pedicular screw 3 along the length of the lateral connection arm 9.

As soon as the surgeon decides that the given vertebra L2 is in the desired position with relationship to the adjacent vertebrae L1 and L3, the surgeon tightens the connections by first the anchorage screws 14, on rod 1, then screws 18, 19 on arm 9, in order to achieve:
on one hand the fixation in rotation of ring 8 on the osteosynthesis rod 1
on the other hand, the fixation in translation and rotation of body 5 of screw 3 on lateral arm 9.

The position of the vertebra L2 to be treated is then firmly maintained mechanically by instrumentation. Of course the second osteosynthesis rod 1A of the instrumentation does not need to be likewise provided with a lateral connection element 4.

The presence of asperities on the whole surface of the rod 1 and the arm 9 allows a quality anchorage of the blockage screws 14, 18 and 19 to be obtained on all points of displacement. These screws act radially on rod 1 and arm 9 by exerting a strong pressure, thereby assuring a favorable connection in rotation and translation.

Connection element 4 according to the invention enables the surgeon to link a rod 1 of an osteosynthesis instrumentation of the COTREL-DUBOUSSET type to a pedicle screw or to a sacral screw, leaving it with complete freedom in the respective position of the two respective axes of the rod and screw (angles and distance). Indeed this system permits a rotation of the vertebra in the horizontal or transverse plane, while letting this vertebra place itself angularly in the sagittal plane without incurring interference constraints, thanks to the degrees of freedom allowed by the mounting. Using two connection elements together provides even greater degrees of freedom by the mountings.

The invention is not limited to the preferred embodiment described, and can include several variants of its implementation.

Thus, instead of being completely closed as represented in the drawing, the ring can be opened or presenting a slot 20 (FIG. 1). The blockage or fixation element such as screws 14 (the number of which can evidently vary while being at least one), then extend through the ring on each side of slot 20. Likewise, anchorage screw 3 can be substituted by a screw similar to the one represented in FIG. 4 of French patent 2,645,732 (89 04 926), having lateral branches of unequal lengths which define a lateral aperture, and no longer a rear opening, for the introduction of arm 9. Clamping member 17 is them obviously modified to accommodate this asymmetrical body. This last type of screw brings a supplementary security in the maintenance of arm 9. Clamping member 17 can likewise be replaced by one of the fixing elements described in French patent 2,645,732.

The pedicle screw linked to the degenerative vertebra can likewise be a closed head screw. It can also be replaced by a spinal hook provided with a channel for receiving connection element 4. This channel could be, like the screw, closed or else upwardly open, and presenting a similar U-shape. The U-shaped head of the hook or the screw, could be closed by a threaded plug such as described in French patent 2,633,177 (88 08 538) of 24 June 1988 filed by Yves Cotrel.

Finally, apertures 13 defined in ring 8 can be in number more or less than those described previously in the preferred embodiment. Advantageously, they can be arranged on the ring so that, whatever the rotation of ring 8 on rod 2 is during the repositioning of the degenerative vertebra by the surgeon, one or several apertures are easily accessible to introduce there a clamping screw on rod 2.

As thus far described, the novel connection element 4 provides means for varying the orientation of the fixation screw, such as screw 5, relative to the primary rod, or rod 1. As explained above, manipulation of the displaced vertebra causes the connection element 4 to rotate and its engagement with the screw 5 to translate along the length of the arm 9 until the vertebra is in its proper position. At that time, the several clamping screws can be tightened to form a rigid construct.

The connection element 4 has been found to be important in another method for fixation of the spine and correction of spinal deformities. In this alternative method, rather than manipulating the vertebra itself into position, the instrumentation is manipulated to adjust the position of the displaced vertebra. In this instance, then, the fixation or anchorage element 3 translates a corrective force to the vertebra, rather than as in the previously described method in which the vertebra transmits a displacement force to the components of the connection element.

In order to facilitate an understanding of this novel method, it is first valuable to understand the biomechanics of the spine and its motion segments, as developed by the present inventor. The term "motion segment" as used herein constitutes adjacent vertebrae and the disc therebetween. First with reference to FIG. 6A, it can be seen that the spine can be divided into three columns along its length—the anterior, middle and posterior columns. The inventor has found that correction of spinal deformities requires consideration of correction in each of these three columns.

Prior art techniques for correcting spinal deformities have tended to focus simply upon one of the three columns, usually the posterior column. For example, the original Harrington system contemplated compression or distraction using posterior instrumentation. Thus, the Harrington instrumentation achieves compression or distraction of the posterior column of the spine, without specific consideration of the impact to the spine in the remaining two columns. In subsequent segmental systems that implement anchorage elements at each vertebral level, again the corrective forces are applied typically in but a single one of the columns, which may lead to difficulties in the other of the columns of the spine.

In other systems, the spine is translated to a rigid rod. Examples of this approach can be found in the Luque Wiring System, sold by Danek Medical, Inc., and the Isola System of AcroMed Corp. These systems provide little control of transverse rotation of the motion segments. A third approach involves engaging a pre-contoured rod to the spine and then rolling the rod to thereby alleviate an abnormal scoliotic curvature. This approach again provided little control over transverse rotation.

Understanding of this new method also requires consideration of the spinal motion segments, or the the relative movement between two adjacent vertebrae and their connecting disk. Proper correction of spinal deformities requires consideration of the biomechanics of the motion segment at each level and particularly requires awareness of how the axes of motion of the segment moves as the segment is subjected to bending, tilting, angularion and rotation. As will be more apparent from FIGS. 6, 7, 8, the axes of the motion segments both rotate and translate. Failure to consider both types of motion may yield inferior correction and may lead to other complications. Accommodating the rotation and translation of the motion segment axes is important to permit separate control of each of the three columns of the spine as well as correction in each of the three planes.

Prior approaches do not account for the complicated biomechanics of the spine. Distraction or compression in prior rod systems utilizing pre-contoured rods tend to place the angle of angularion of the spinal segment far removed from the true axis of the motion segment. Typically, this axis of angulation in prior systems is in the pedicle into which time screw is inserted and not at the level of the disc, deformity or injury. As can be seen from the following discussion, this approach is contrary to the normal biomechanics of the spine.

Figure 6A:
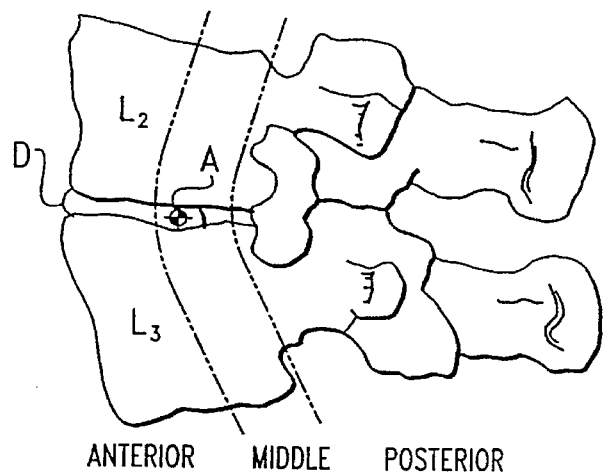
FIGS. 6A–c are side schematic representations of a spinal motion segment depicted in the sagittal plane and showing the location of the axis of the segment during normal movement of the spine.
Figure 6B:
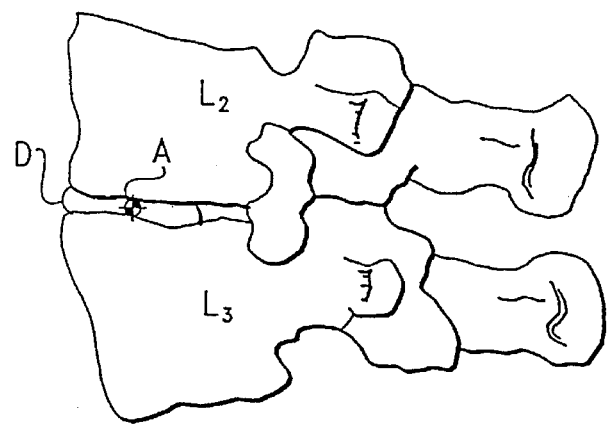
Figure 6C:
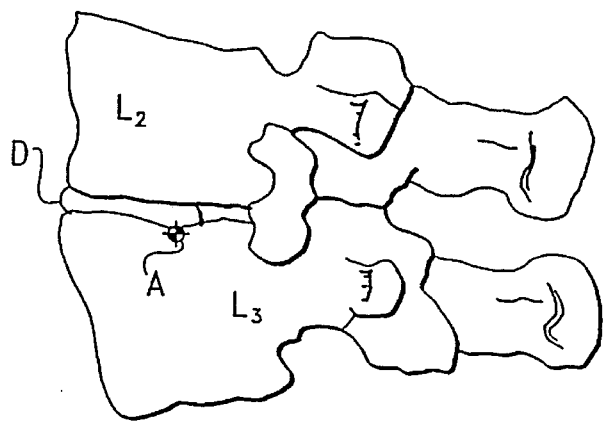

Referring first to FIGS. 6A–6C, a spinal motion segment is depicted in the sagittal plane. In FIG. 6A, the neutral position of the motion segment is shown in which the axis A is located in the middle column and posteriorly and inferiorly in the disk. In the sagittal plane, the motion segment is subject to angulation in which the adjacent vertebrae rotate relative to each other. In the case of flexion, as shown in FIG. 6B, the axis A moves anteriorly and superiorly into the center of the disk. On the other hand, in extension, as shown in FIG. 6C, the axis moves posteriorly and inferiorly slightly below the inferior endplate of the disk. It is thus apparent that the axis of each spinal motion segment translates with angulation in the sagittal plane.

The same phenomenon is exhibited in the frontal plane, as shown in FIGS. 7A and 7B. In FIG. 7A, the neutral position of the axis A is along the midline of the spine and somewhat below the center of the disk close to the inferior endplate. With the inferior vertebra held stationary, the superior vertebra can bend laterally, or tilt, to the right or to the left. A tilt to the right is depicted in FIG. 7B, in which it is seen that the axis A moves not only laterally to the left but also somewhat cephalad into the disk. A tilt to the left would product an opposite lateral movement of the axis with a similar cephalad movement. Again, the axis of the motion segment translates in the frontal plane.

Finally, the vertebrae appear in the transverse plane in FIGS. 8A and 8B. In the neutral position shown in FIG. 8A, the axis A is disposed generally in the centroid of the neural canal C. With rotation to the right or left, the axis A always remains within the neural canal, as shown in FIG. 8B for rotation to the right. The axis does shift laterally somewhat in a direction opposite to the rotation, but nevertheless always remains within the canal. This is an important aspect of proper motion of a spinal motion segment since maintaining the axis of the motion segment within the neural canal is protective of all of the neural elements passing therethrough. It is believed that many prior systems and techniques for correction of spinal deformities have a tendency to displace the axis out of the canal leading to an increased risk of damage to the neural elements. It can be seen from this view in the transverse plane that the vertebral motion segment has a very narrow window of movement before the axis of the segment leaves the canal C. Any correction applied to the spine that does not take into account the aspects of rotation in the transverse plane of a motion segment carries the risk of damaging the neural elements housed within the canal.

From the foregoing FIGS. 6–8, it can be seen that every segmental spinal motion segment involves both translation and rotation in each of the three planes (sagittal, frontal and transverse). Thus, in the frontal plane, the motion segment can translate up and down and left to right, and can rotate or tilt left or right. In the sagittal plane, the segment can translate up and down and posteriorly and anteriorly, while it can rotate, or more particularly angulate, in flexion or extension. Finally, in the transverse plane, the motion segment biomechanics yields translation to the right or left, or anteriorly or posteriorly, and rotation to either the right or left, again always maintaining the axis within the neural canal.

With this explanation of the movement of the spinal motion segments, it can be appreciated that optimum correction of spinal deformities should permit the motion segments to move in the manner for which they were designed. In relation to the three spinal columns discussed above, it is also important to control the correction of the deformity by keeping the motion segment axes between the longitudinal implant, or rod, and the middle spinal column, or close to the neural canal. With the present technique, it is possible to achieve elongation or distraction of the anterior and middle columns anterior to the motion segment axis, and approximation or compression of the posterior column behind the axis. In accordance with the present invention, the surgeon, and not the instrumentation, determines the location of the motion segment axes.

A further feature of the invention provides the means for achieving this optimum segmental and global correction of the spine. More particularly, the invention contemplates in situ contouring of a longitudinal spinal implant when it is engaged to several vertebral bodies by screws or hooks. While the longitudinal implant may be a plate or bar, the present embodiment contemplates the use of a spinal rod, such as previously described. Contouring the rod alone is not sufficient and will frustrate the normal movement of the three columns of the spine and the spinal motion segments. Specifically, in situ contouring of a rod rigidly engaged to the spine will simply translate the vertebrae without considering the needs of the motion segment axes explained previously.

Thus, a further aspect resides in connecting the vertebral fixation elements, such as bone screw 3, to the rod, such as rod 1, in a manner that permits free rotation and translation of the vertebra to which the bone screw is attached relative to the rod as it is being contoured. This capability is achieved by the collar or ring 8 engaged to the rod 1, as well as the cylindrical fixing element 17 engaged to the arm 9 of the ring 8. As previously described, each of these components is free to translate and rotate relative to the component to which they are engaged. In this manner, as the rod is contoured, corrective forces are applied to the vertebral segment while the free degrees of rotation and translation permit the vertebra to seek its proper biomechanical orientation. In addition, this approach accommodates the needed and necessary translational and rotational degrees of freedom in each of the three planes of a spinal motion segment.

Figure 9A:
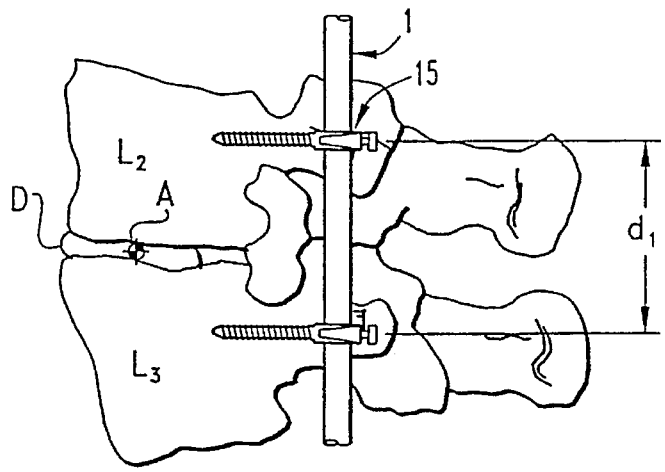
FIGS. 9A–C are schematic representations of a motion segment viewed in the sagittal plane in which the segment is instrumented with a longitudinal implant that is contoured in situ in accordance with the principles of the present invention.

This inventive approach to instrumentation of the spine and correction of spinal deformities can be readily understood from a few diagrammatic representations. Referring first to the examples in FIGS. 9A–9C, in situ contouring of the rod in the sagittal plane is depicted. It is understood that the system can be generally constructed as illustrated in FIG. 3, such as by implementing a rod 1 engaged to the vertebrae by way of a bone screw assembly 15. The construct in FIG. 9A represents the uncorrected position of a spinal motion segment. In this position, the bone screw assemblies 15 are displaced from each other by a distance $d_1$. In this arrangement, the axis A of the motion segment is located in the middle of the disk D, similar to the position illustrated in FIG. 6B. In order to restore the segment to its proper position or alignment, and in order to exert a proper and precise biomechanical force for this correction, it is necessary that the axis P along which the corrective force is applied be able to translate in the anterior/posterior direction.

Figure 9B:
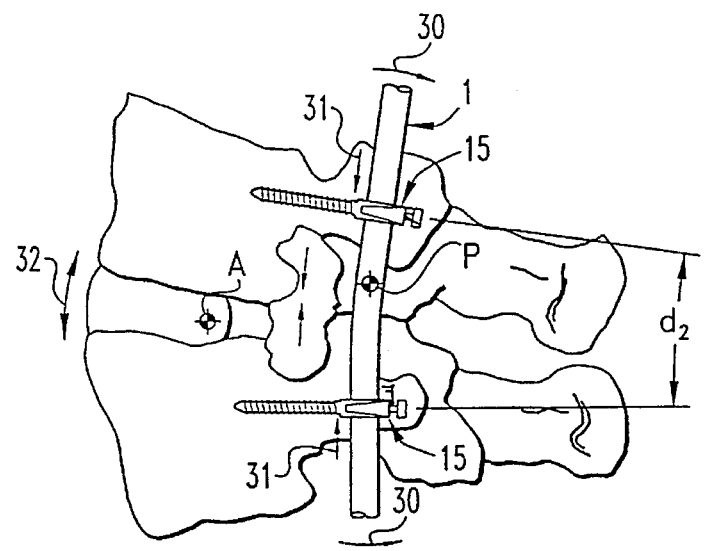

This neutral position is shown in FIG. 9B which shows the spinal motion segment after application of a bending force to the rod 1. This bending force is applied between the two bone screw assemblies 15 so that the rod 1 is essentially bent around pivot point P, with the ends of the rod moving in the direction of the arrows 30. In order that the axis A be permitted to translate, it is necessary that the bone screw assemblies 15 be able to slide along the rod 1 in the direction indicated by the arrows 31. Permitting this free translation of the screw assemblies 15 along the rod 1 allows the anterior disk space to open or elongate in the direction of the arrows 32. Some compression of the posterior disk space may also occur. In this instance, contouring the rod 1 while permitting sliding movement of the screw assemblies 15 leads to a decrease in the distance between the screws, as represented by the distance $d_2$, which is less than their original uncorrected distance $d_1$. It can further be seen that the axis A is now situated in its proper neutral position as shown in earlier FIG. 6A.

Figure 9C:
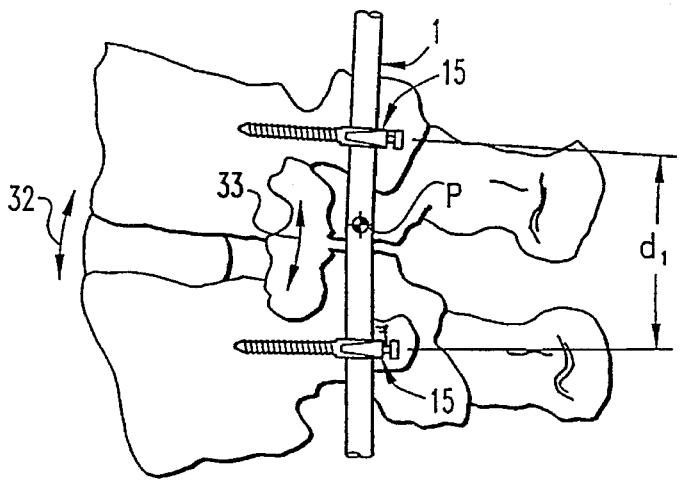

The in situ contouring principles according to this invention also contemplate contouring the rod 1 with the screw assemblies 15 fixed to the rod, as shown in FIG. 9C. In this instance, the distance measured along the rod between the two screw assemblies 15 remains constant as distance $d_1$. Contouring the rod 1 about the pivot point P not only produces distraction at the anterior part of the disk, as represented by arrows 32, but also distraction at the posterior part of the disk as represented by arrows 33. This procedure may be important to open up the disk space, such as to decompress the disk D.

It is also contemplated that both steps 9B and 9C can be implemented to not only to control the axis A relative to its proper neutral position, but also to open up the neuroforamina as required. Therefore, the rod 1 can be contoured slightly with the screws 15 free to translate along the rod. Subsequently, the screw assemblies 15 can be fixed to the rod and further contouring of the rod 1 be accomplished to open up the neuroforamina. It is understood that with any spinal instrumentation, it is important that the neuroforamina remain open to avoid trauma to the spinal cord. In the preferred procedure to address this concern, the screw assemblies are alternately locked and released on the rod, and the rod contoured with each type of fixation to achieve an "averaged axis" in the sagittal plane with respect to the bending axis P. By this it is meant that the axis P at which the contouring force is applied is maintained as close to the neural canal as possible to avoid compromise to the neuroforamina. Typically, the "averaged axis" will reside posterior to the disc and anterior to the longitudinal implant or rod. Under ideal circumstances, the longitudinal implant or rod would extend along the length of the spine through the neural canal. Since this is naturally not possible, the present in situ contouring principles allow the "averaged axis" of the rod to be manipulated as close to the neuroforamina as possible.

With this example, many beneficial aspects of this inventive method can be discerned. It should first be pointed out that this in situ contouring approach can be implemented with any longitudinal implant, such as rod, bar or plate. Optimum application of the in situ contouring technique requires that the osteosynthesis implant, such as rod 1, be a stiff, strong and ductile one. This reference to a stiff strong ducthe implant encompasses many mechanical properties. It is important that the implant be able to be bent without elastically springing back completely or partially to its original position. Thus, while time rod 1 must be ductile enough to be bent in situ, must be stiff or inelastic enough to avoid this "springback" effect. Finally, the rod 1 must be strong to support the biomechanical corrective forces being applied to the vertebrae. One rod-type longitudinal implant has been found that fulfills each of these requirements, namely the Cotrel rod which forms part of the Compact Cotrel-Dubousset (CCD) system sold by SOFAMOR, S. A., of Rang du Fliers, France.

Figure 10:
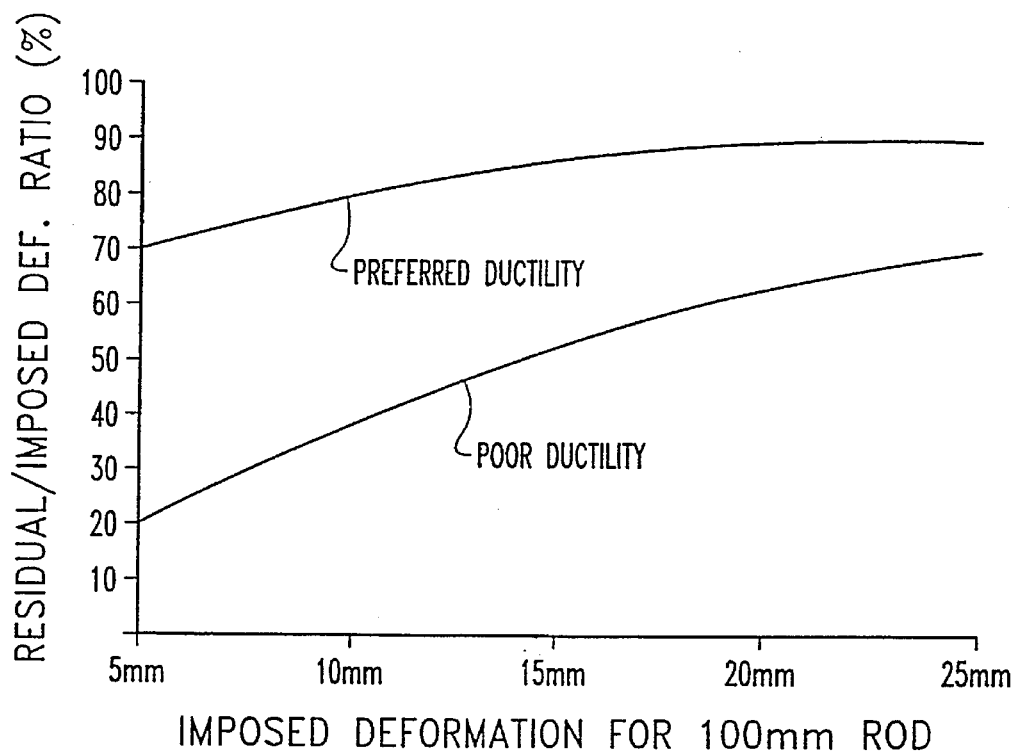
FIG. 10 is a graph of ductility for the material of the longitudinal implant used in the in situ contouring technique. 5

Other longitudinal implants can be acceptable, such as the Superflex rod sold by Danek Medical as part no. 808-088. The CCD rod, such as the CCD 7 mm hyperquench rod, is formed of 316LVM low cold worked stainless steel. The preferred implant material has the strength of the low cold worked stainless with the requisite ductility. One measure of this ductility is the "springback" of the material, which can be expressed in terms of the ratio between the residual and the imposed deformation of an implant. This ratio is known to vary as the imposed deformation varies, as reflected in the graph in FIG. 10. An optimum implant material will exhibit a "springback" ratio of nearly ninety percent (90%) at imposed deformations of 20 mm or more.

It has been found that implants with higher "springback" ratio curves, i.e., that are more ductile, are better suited for the in situ contouring principles of the present invention, due, in part, to the limited space available at the site of the instrumentation for "over-bending" the implant. It is, of course, preferred that the implant maintain its imposed deformation, but it is understood that this "perfect" ductility arises at a sacrifice to strength. The aforementioned spinal rod products exhibit the best known blend of ductility and strength for the in situ contouring procedure.

It should be appreciated that the illustrated in situ contouring technique, as enhanced by free sliding movement of the bone screw assemblies 15 relative to the rod 1, allows the spinal motion segment freedom of, movement in rotation and translation in each of the three planes of motion of the segment. This approach also permits optimum correction of the spine in each of the three spinal columns. With this approach, that is in situ contouring with the screw assemblies inserted through the pedicles into the anterior vertebral bodies, the screws are used as much for application of corrective forces as they are for ultimate fixation of the system.

The method permits the greatest possible flexibility to the surgeon to adjust the location of the axis A of the vertebral motion segment simply by selection of the manner in which the rod is bent and the fixity of-the screw assembly 15 to the rod 1. For instance, in the illustrated embodiment of FIG. 9B, rod benders are applied directly adjacent each other at the pivot point P. Alternatively, the rod 1 can be bent immediately adjacent a single screw, by placing the rod benders on both sides and close to the head of the screw assembly, rather than between the screw heads. In this instance, the specific screw will translate in the sagittal plane but not angulate, and the particular vertebra will translate without rotation. The pivot point P can also be shifted toward one screw assembly or another to impart a differential angulation between adjacent vertebrae.

These in situ contouring principles can be applied for correction or contouring anywhere along the spine. For instance, kyphotic contouring in the sagittal plane can be achieved by angulating or flexing the screws in a motion segment and dorsally or posteriorly translating the segment where needed. Lordotic contouring in the sagittal plane, used to correct kyphosis, can restore the segmental lordosis where needed without compression, thereby avoiding disk loading and closing of the neural foramen. Lordotic contouring with the screw assemblies 15 unlocked and then locked on the rod can result in an "averaged axis" of angularion situated between the back of the disk and the front of the rod, that is somewhere within the spinal canal. Thus, this lordotic contouring gives three column control with selective segmental elongation of the spine anteriorly to the desired axis, and segmental approximation of the posterior column behind the axis. The segmental approximation of the posterior column is beneficial for posterior fusion.

It can also be appreciated that this in situ contouring with free movement of the fixation assembly on the rod, can correct tilt of a given vertebra in the frontal plane (see FIGS. 7A–7B). In particular, the screw assemblies 15 are not only free to translate along the length of the rod but also free to rotate about the rod. As the rod 1 is contoured in situ, the motion segment tends to seek its neutral axis in all three planes. Thus, a given vertebra may tend to tilt in the frontal plane, which movement is permitted because its fixation screw assembly 15 is able to turn in the pedicle of the vertebra.

It has been found that translation of the spine in all three planes achieved by the in situ contouring principles is enhanced by use of the lateral connection element 4 previously described. To control torsion or rotation of the spinal motion segment in the transverse plane requires force application anterior to the axis of rotation. This force application is possible with screws advanced through the pedicles from a posterior approach. However, this approach requires the transverse connection element 4 and the freedom of rotational and translational movement of the fixation screw relative to the element 4, and of the element 4 relative to the osteosynthesis rod 1.

In the past, the deformed spine has been translated to a rigid pre-contoured longitudinal implant. In another technique, a pre-contoured longitudinal implant is engaged to the spine and then the implant is rolled within the patient, ostensibly correcting the spinal deformity. However, this technique of rolling the rod leading to torque transference towards the ends of the instrumentation can be problematic and a contributor to spinal decompensation. Moreover, rolling the rod does not control much rotation of the spine in the transverse plane, and may actually increase torsion in the spine to contribute to an already existing rotational deformity through force applications acting posterior to the axis of rotation in the transverse plane. The present invention addresses these problems with prior art systems.

In particular, this invention recognizes that the vertebrae must be able to angulate in the sagittal plane, as well as translate anteriorly or posteriorly in this plane. The vertebrae must likewise be able to translate and rotate in the transverse plane, which plane, is most affected by controlled torsion of the rod 1. Without this freedom of movement, that is with all the components rigidly fixed together, the spine will bind and will not correct segmentally when torsion is applied to the rod. These principles are illustrated in FIGS. 11A and 11B. A spinal rod 1 extends on one side of the spine and is engaged at its ends by way of bone screw assemblies 15 to vertebrae adjacent to the displaced vertebra. The construct includes a lateral connection element 4, in which the ring 8 of the element is clamped to the rod 1. A bone anchorage element 3 is engaged through the pedicle and into the anterior body of the displaced vertebra. This anchorage element, or screw 3, is engaged to the arm 9 of the lateral connection element 4. This assembly is identical to the assembly shown in FIG. 3.

As with the prior described assembly, the anchorage screw 3 is free to translate and rotate along the arm 9. In this construct, a corrective torsional force 35 is applied to the rod 1 so that the lateral connection element 4 rotates in the direction of the arrow 36. As the rod 1 is rotated, the arm 9 also pivots in the direction of arrow 37 which causes the affected disk to move in the direction of arrow 38 toward its proper position. The corrective force that moves the vertebra back to its position is applied through the arm 9 and through the anchorage screw 3 directly into the vertebra. Since this correction in the transverse plane requires both rotation and translation of the axis of the motion segment, the anchorage screw 3 must be free to translate along the arm 9. Thus, the screw 3 will translate in the direction of the arrow 39 toward the end of the arm 9 as the affected vertebra assumes its correct position relative to the adjacent vertebrae. Once the vertebra has been properly positioned in the transverse plane, the anchorage screw 3 is locked onto the arm 9 of the lateral connection element 4 to complete this aspect of the construct.

It should, or course, be understood that the screw assemblies 15 are not rigidly clamped to the rod 1, so that these assemblies operate as a bearing for the torsional movement of the rod 1. One significant benefit of this approach is that unlike prior systems this direct derotation still permits subsequent segmental sagittal plane angulation, which is necessary to correct the motion segment in the sagittal plane. This described approach for direct derotation produces a rotation/translation of the vertebra to be treated.

The lateral connection element 4 and the many degrees of freedom provided by the system shown in FIGS. 11A and 11B permits great flexibility in the application of corrective forces to the spine. For instance, the lateral connector element 4 can be free to rotate around the rod, and the anchorage screw 3 free to rotate and translate along the arm 9 of the lateral connection element 4.

The tools to achieve the in situ contouring of the osteosynthesis rod 1 are depicted in FIGS. 12–16. Bending irons of known design can be used in some applications to contour the ductile rod in situ. However, it has been found that since the bending of the rod occurs within the patient using in situ contouring, the anatomical restrictions have dictated the development of new tools. For example, the L-bender shown in FIGS. 12A and 12B are configured for corrections ill the frontal plane. Specifically, the L-bender 40 includes a long lever arm 41 that is manipulated by the surgeon, a right angle beard 42 at one end of the arm 41 leads to the gripper arm 43. At the terminal end of the gripper arm 43 is a groove 44 defined therein to receive the osteosynthesis rod 1 therein. As can be seen from FIG. 12A, the groove 44 is oriented at an angle relative to the plane of the lever arm 41, more particularly because the gripper arm 43 is itself angled upward at the right angle bend 42. Left and right L-benders are provided with the gripper arm 43 and groove 44 oriented 90° opposite from that shown in FIGS. 12A–12B. Thus, the surgeon can place two L-benders immediately adjacent with the lever arms 41 diverging to provide room for the arms to be manipulated to contour the ductile rod.

The L-bender 40 can also be used to facilitate alignment and connection of the various implants as they are being inserted into the patient. In usage, the fulcrum for the bending force applied to the rod is at the base of the bender 40, that is at the right angle bend 42. With the long lever arm 41, significant but controlled forces can be applied to bend the rod with less effort.

It has also been found that contouring rods at any time can cause indentations on the rod, which can ultimately lead to early fatigue or fracture. The rod grip bender 45 depicted in FIGS. 13A–13B addresses this problem. The rod grip bender 45 includes a pair of jointed arms 46 and 47, which terminate beyond the pivot joint in a pair of aperture halves 48 and 49. The aperture halves 48 and 49 are configured to receive and grip the osteosynthesis rod 1 therein when the arms 46 and 47 are closed together. A locking mechanism 50 is provided at the opposite end of the arms 46 and 47 to lock the arms relative to each other, and to thereby lock the rod grip bender to the rod to be contoured.

Figure 15A:
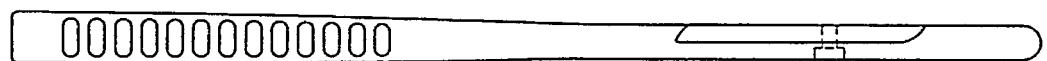
FIGS. 15A–B are side and top elevational views of a counter-rotator tool for use in direct derotation of spinal instrumentation.
Figure 15B:
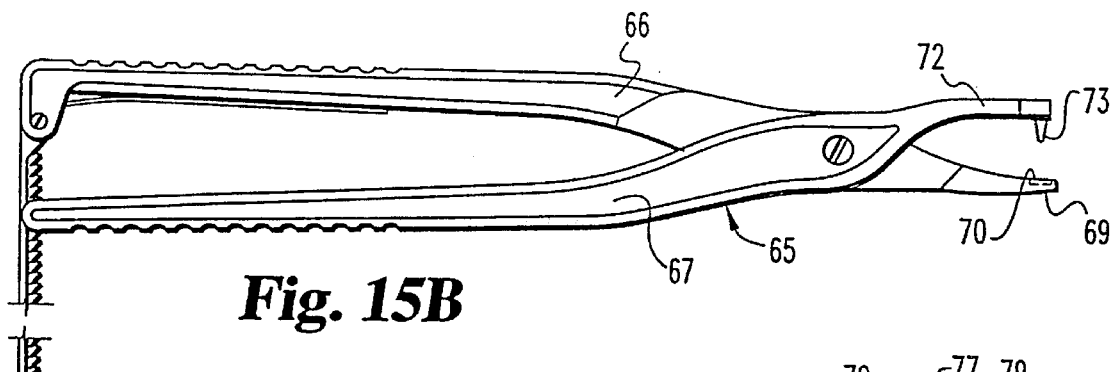
Figure 16:
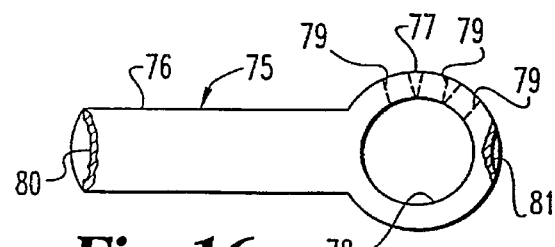
FIG. 16 is a top elevational view of a lateral connection element modified for use with the tools shown in FIGS. 14–15.
Figure 12A:
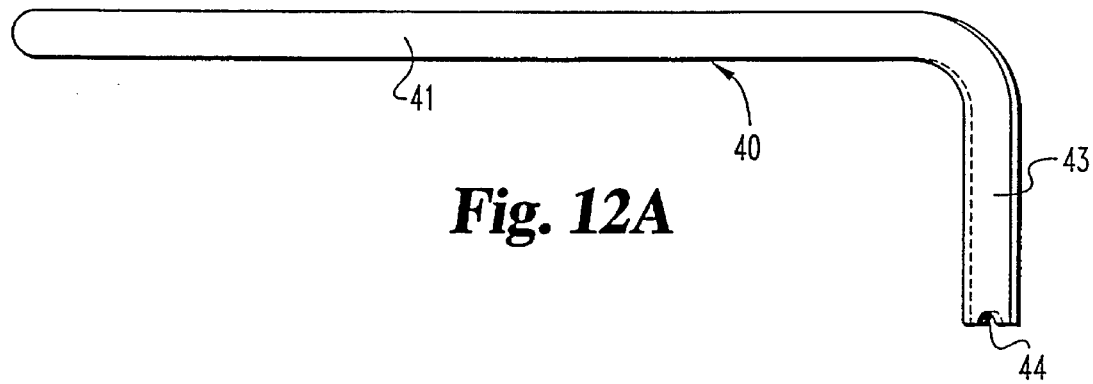
FIGS. 12A–B are top and side elevational views of an L-bender for use in in situ contouring of a longitudinal implant.
Figure 12B:
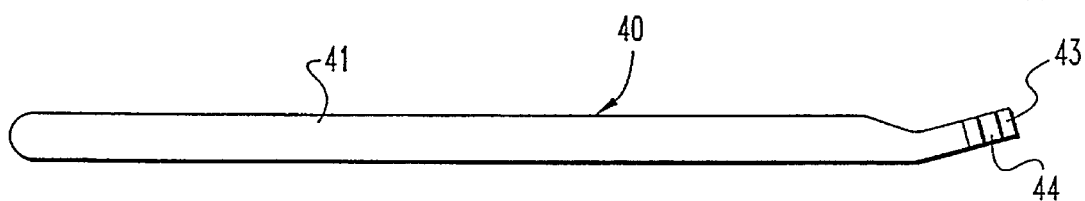
Figure 13A:
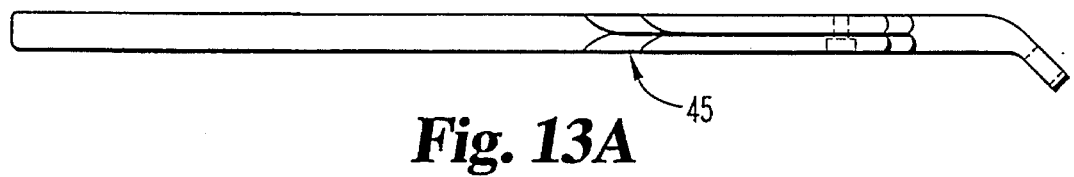
FIGS. 13A–B are side and top elevational views of an rod grip bender for use in situ contouring of a longitudinal implant.
Figure 13B:
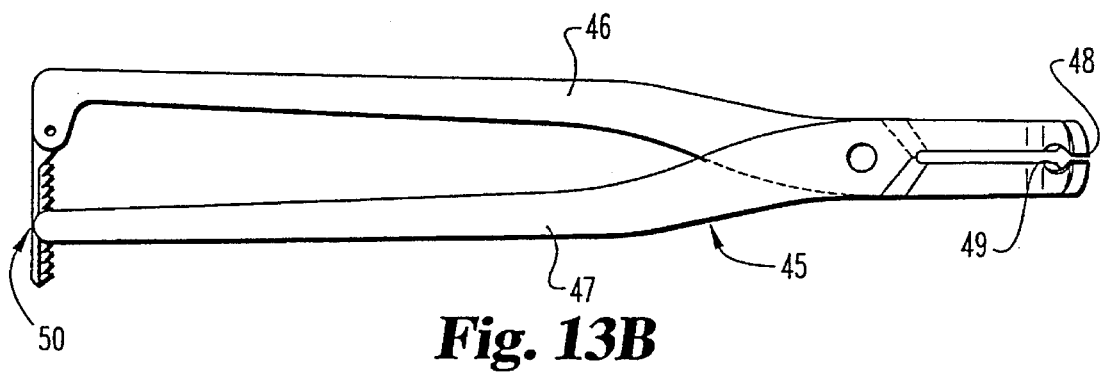

Two other tools useful in performing in situ contouring of the rod are the traction rotator 52, shown in FIGS. 14A–B, and the counter-rotator 65, shown in FIGS. 15A–B. The traction rotator 52 and counter-rotator 65 are configured to engage a lateral connection element which is of modified design with respect to the connection element 4 described above. This modified lateral connection element 75, depicted in FIG. 16, is in many respects similar to the element 4. For example, the element 75 includes an arm 76 radially extending from a ring 77. The ring 77 has an aperture 78 sized to receive the spinal rod 1 therethrough. A number of threaded apertures 79 are provided to receive set screws in the same manner as the connection element 4 shown in FIG. 1. The primary modification presented by the lateral connection element 75 is the provision of a dimple 80 in the free end of the arm 76, and a corresponding oppositely located dimple 81 in the ring 77. The purpose of these dimples 80 and. 81 will be explained in connection with the rotator 52 and counter-rotator 65.

The traction rotator 52 is configured to rotate the lateral connection element 75 relative to the rod 1, while also permitting traction of an anchorage screw such as a screw 3, relative to the arm 76 of the lateral connector element. The traction rotator 52 includes a pair of arms 53 and 54 pivotably mounted near the gripping end of the arms. As with the rod grip bender 45, the arms include a locking mechanism 55 for locking the arms relative to each other.

The working end of the traction rotator 52 is configured to grip the ring 77 of the lateral connection element 75 to allow it to be rotated relative to the rod 1. Thus, the terminal end of arm 54, namely end 56, may include a pair of arms 57 separated by a slot 58 to cradle opposite sides of the ring 77, or the head of the spinal screw mounted on the arm 76. The other arm 53 terminates at its end 60 in a projection 61 which is is adapted to extend into the dimple 81 formed in the ring 77. Thus, this traction rotator 52 provides means for engaging the ring 77 of the lateral connection element 75 so that it can be rotated relative to the rod 1. Moreover, as seen in FIG. 14B, the ends 56 and 60 of the traction rotator 52 are configured to extend around from one side of the rod to the other to permit application of a traction force to the rod, even as the rod is rotated. The tool 52 does not interfere with the free sliding motion of the anchorage screw along arm 76 of the lateral connection element 75. Thus, where the correction requires rotation and translation of the vertebra to be treated, use of the traction rotator 52 permits free movement of the bone screw as the vertebra seeks its anatomic neutral position.

The counter-rotator 65 primarily operates as an anchor at one level when the traction rotator 52 is being manipulated at a higher level. The counter-rotator 65 includes a pair of arms 66 and 67 pivotably engaged near their respective ends. The arm 66 includes a working end 69 having a recess 70 formed therein. This recess 70 is configured to receive the free end of arm 76 of the lateral connection element 75. Opposite the recess 70, on the working end 72 of arm 67, is a projection 73, which is similar to the projection 61 of the traction rotator 52. This projection 73 is configured to engage the dimple 81 in the ring 77 of the lateral connection element 75.

Figure 17A:
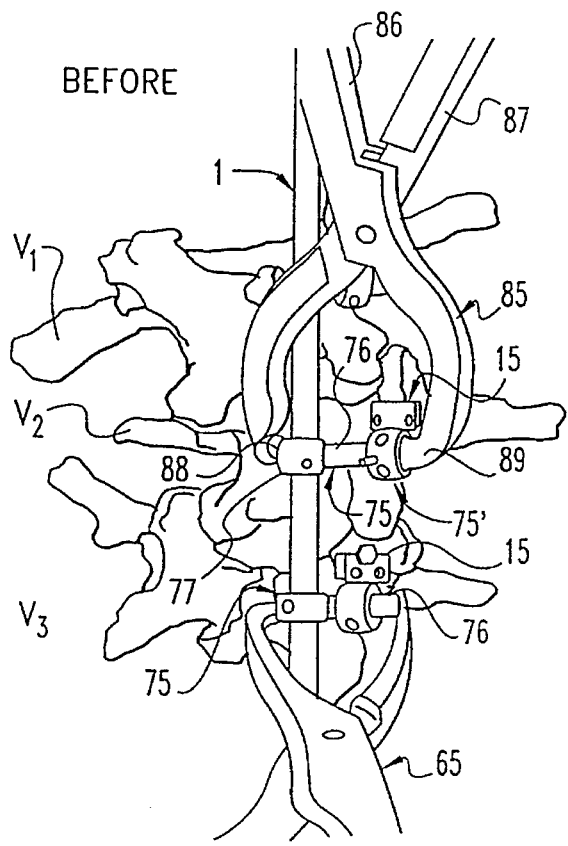
FIGS. 17A–B are anterior views in the frontal plane of three vertebrae in which one displaced vertebra is restored to its proper anatomic position by direct derotation.
Figure 17B:
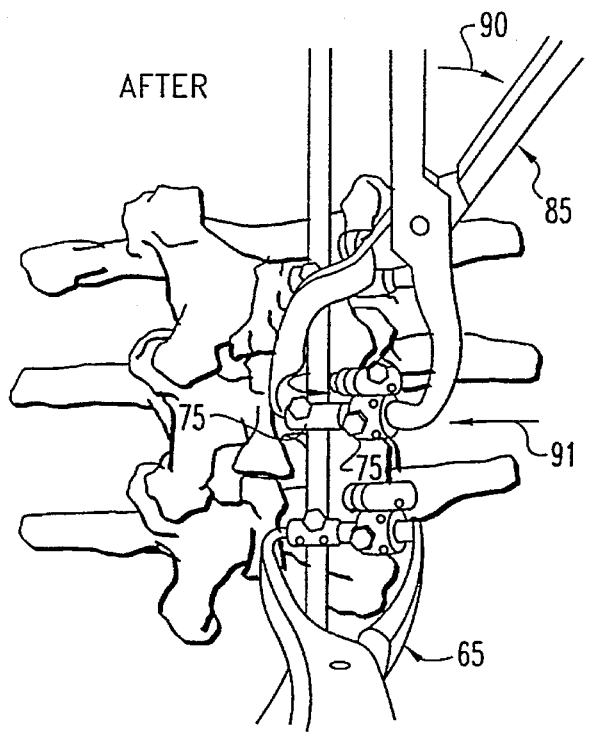
Figure 18A:
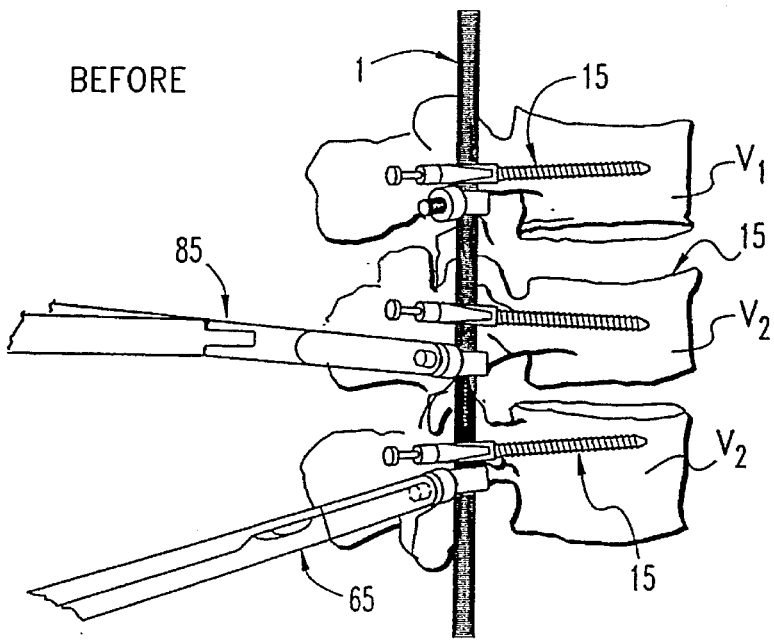
FIGS. 18A–B show in the sagittal plane the direct derotation depicted in FIGS. 17A–B.
Figure 18B:
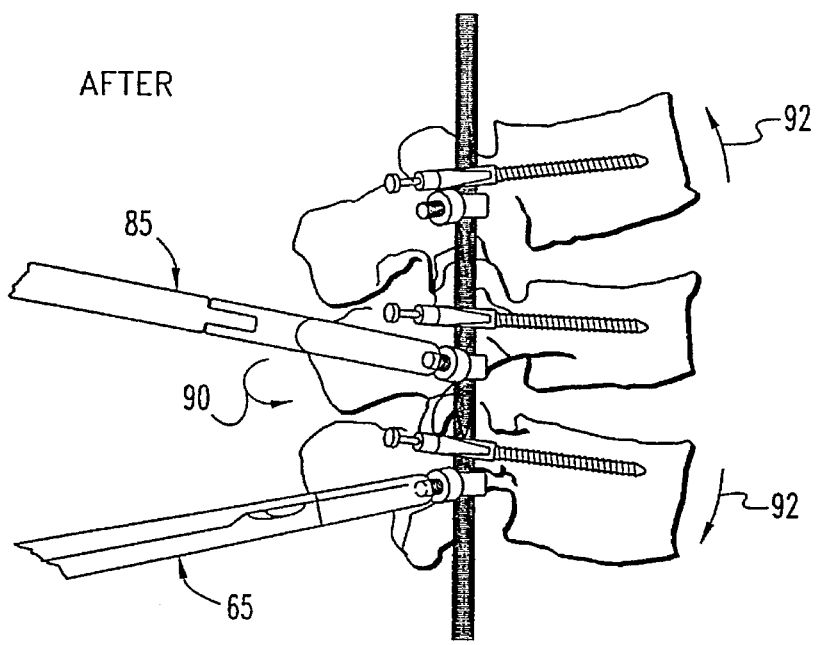
Figure 19A:
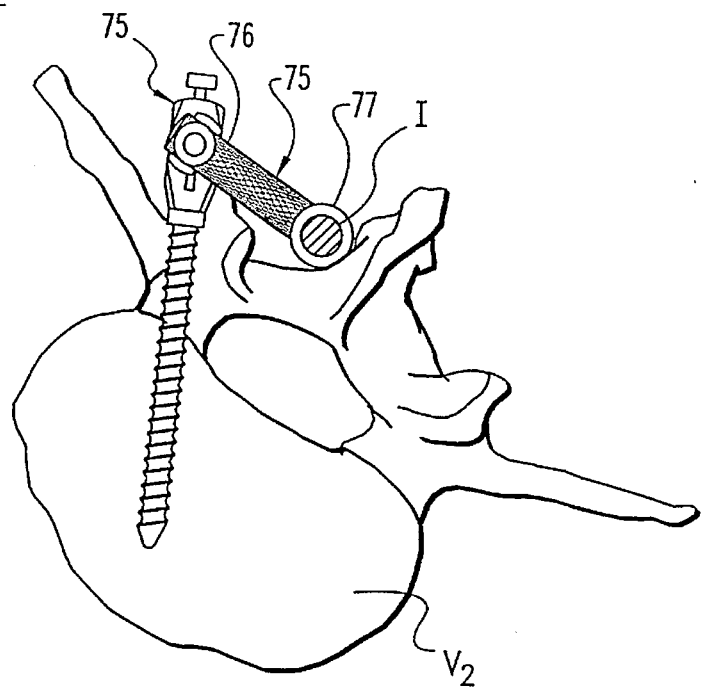
FIGS. 19A–B show in the transverse plane the direct derotation depicted in FIGS. 17–18.

The manner in which the foregoing tools 52 and 65 are used is depicted in FIGS. 17–19. Each set of figures represents "before and after" representations of the motion segments as viewed from the frontal, sagittal and transverse planes. First, with reference to FIG. 17A, a modified traction rotator tool 85 is shown. This tool is the substantial equivalent of the tool 52 shown in FIGS. 14A–B in that it includes hinged arms 86 and 87, with the working end of arm 87 terminating in a projection 88. The projection 88 is configured to be received within a dimple 81 in the ring 77 of a lateral connection element 75. The traction rotator 85 is modified in that the working end of the second arm 86 includes a barrel 89 formed at the end of the arm. The barrel 89 is sized to receive the arm 76 of the lateral connection element 75. This barrel 89 is a substitute for the forked arms 57 of the rotator 52. As shown in FIG. 17A, the barrel 89 is slidably received over the free end of the arm 76 of the lateral connection element 75. The barrel 89 is of sufficient depth to allow the barrel to move significantly along the length of arm 76.

As shown in FIGS. 17–18, the instrumented vertebrae are labeled $V_1$–$V_3$, with the middle vertebra $V_2$ being misaligned. The object, then, is to reorient the middle vertebra to bring it into alignment with the vertebrae $V_1$ and $V_3$. This object can be accomplished by orienting a longitudinal implant, such as rod 1, along the spine. A bone screw assembly 15 is engaged into each vertebra, as shown most clearly in FIG. 18A. Each bone screw assembly 15 is connected to the rod 1 by way of a pair of lateral connection elements 75 and 75'. In each pair, the ring 77 of one element is threaded onto the rod 1, while the ring of the other element 75' is threaded onto the arm 76 of the first element. The arm 76 of the second lateral connection element 75' extends generally parallel to the principal rod 1.

In the illustrated procedure, a counter-rotator 65 is used to grip the lateral connection element 75 of the lowest vertebra $V_3$ in the manner described above. The bone screw assembly 15 at this level can be rigidly fixed to its corresponding lateral connection element. However, the components instrumenting the middle vertebra $V_2$ are engaged but remain loose so that the components can translate and rotate relative to each other, in the manner described above in connection with the in situ contouring principles. The traction rotator 85 is then used to grip the ends of the lateral connection element 75, with the barrel 89 sliding over the arm 76 until it contacts the second lateral connection element 75' to which the bone screw assembly 15 is attached.

The correction is accomplished by holding the counter-rotator 65 generally rigid, which thereby holds the vertebra $V_3$ and the rod 1 generally immobile. Next, the traction rotator 85 is rotated in the direction of the arrow 90 in FIGS. 17B, 18B and 19B, or away from the spinous process. The goal of this rotation is to manipulate the displaced vertebra $V_2$ back into its proper orientation. As the traction rotator 85 is pivoted, the lateral connection element 75 that is engaged by the rotator also rotates about the rod 1. The second lateral connection element 75' that supports the bone screw assembly 15 also rotates about the arm 75 of the first connection element 75. As described above, the manipulated vertebra $V_2$ will automatically seek its proper position, provided the fixation components are free to translate and rotate relative to the fixation rod 1. The vertebra $V_2$ is rotated because the rotation applied by the traction rotator 85 is translated through the lateral connection elements 75 and 75', through the bone screw assembly 15 and into the vertebra.

It can be appreciated that as the vertebra $V_2$ moves toward its aligned position, the bone screw assembly 15 moves relatively laterally, closer to the rod 1. Thus, the second lateral connection element 75' will automatically slide along the arm 76 of the first connection element 75 in the direction of the arrow 91 in FIGS. 17B and 19B. The barrel 89 of the traction rotator 85 is maintained in contact with the second lateral connection element 75' by squeezing the arms 86 and 87 of the tool 85 together. Alternatively, translation of the element 75' along the arm 76 can be forced by compressing the tool as it is rotated.

This direct derotation of the spine as thus far described contemplates using the traction rotator 85 with the barrel 89 engaged over the at, 75. However, these same direct derotation principles call be accomplished using the traction rotator 52 shown in FIGS. 14A–B. In this instance, the forked arms 57 would directly contact the ring of the second lateral connection element 75'. Since the ring of the second element 75' will slide along the arm 75 of the first connection element 75, the arms 53 and 54 of the traction rotator 52 must naturally be gradually closed together until the derotation is complete.

Figure 19B:
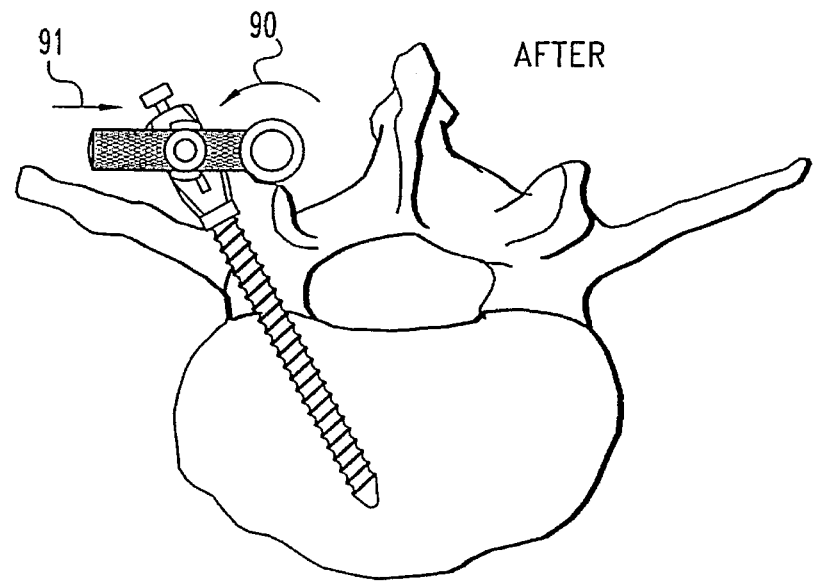

By comparing the sets of "before and after" figures, it can be seen that the vertebra $V_2$ translates laterally (FIG. 17B) and rotates (FIG. 19B). Moreover, the adjacent vertebrae $V_1$ and $V_3$ angulate in the sagittal plane, as represented by the diverging arrows 92, so that all of the vertebrae assume their proper anatomical orientation.

The traction rotators 52 and 85, and the counter-rotator 65 provide another means for correcting spinal deformities by direct derotation of the vertebra to be treated. It is contemplated that this direct derotation can be used in conjunction with in situ contouring to achieve complete correction of deformities in all three planes and in all three spinal columns. A typical procedure may, for example, involve using the rotators and counter-rotators to derotate one or more badly misaligned vertebrae. This direct derotation would then be followed by in situ contouring of the longitudinal implant to effect correction of the remaining deformities. Preferably, the direct derotation and in situ contouring will progress from the lowest level of instrumentation to the highest. While the entire spine is being corrected, the present invention permits segmental correction, that is, correction limited to one motion segment at a time. This segmental procedure allows each vertebra to seek its proper anatomic position without compromise and without closing the neural canal. It is anticipated that the sequential segmental correction may be repeated from bottom to top until the spine is nearly perfectly aligned.

Figure 20A:
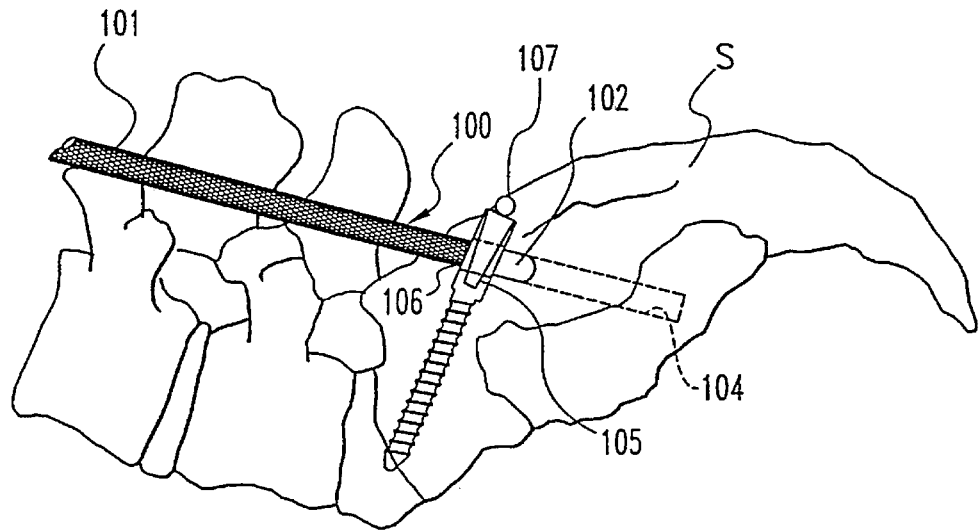
FIGS. 20A–B are side elevational and top perspective views showing the sacral fixation techniques and "iliac buttress" of the present invention.
Figure 20B:
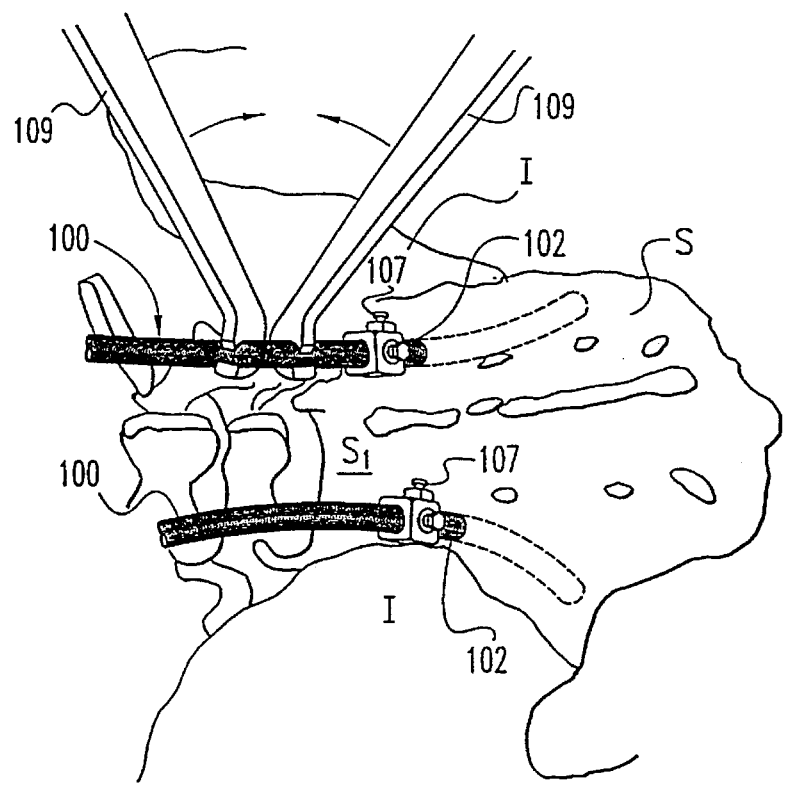

In many instances, correction of a spinal deformity requires anchoring the inferior end of the rod construct in the sacrum. Various systems for sacral fixation are known in the art, but do not contemplate a system adapted for in situ contouring or that will significantly resist pullout of the sacral screws. In another aspect of the invention, an intrasacral fixation construct is depicted in FIGS. 20A–B. This intrasacral fixation involves three concepts. In the first, an osteosynthesis rod 100 is implanted along the spine in which the greatest portion 101 of the rod bears surface asperities, as on rod 1 described above. This portion 101 is used for fixation to the upper vertebrae of the spine in a manner as set forth in the earlier described embodiments. The inferior end 102 of the rod can include the asperities, or can be smooth for insertion into a bore 104 formed in the lateral sacral mass. In the preferred embodiment, this bore 104 is slightly curved, as shown in FIG. 20B.

The rod 100 is supported not only by the portion 102 engaged in the sacrum, but also by a sacral screw 105 that enters the superior portion of the sacrum at an angle, in the second concept of this inventive feature. In the preferred embodiment, this screw 105 extends through the subchondral bone of the sacrum and through the L5-S1 disc endplate, as can be seen in FIG. 20A. The screw 105 includes an oblique canal 106 for reception of the rod 100 therethrough. The rod 100 is clamped within the oblique canal 106 by one or more set screws 107 or other locking mechanism. The canal 106 may be oriented at a number of angles relative to the axis of the screw 105 as dictated by the anatomy.

The head of the screw 105 is preferably buried into the bone to reduce the external profile of the implant and to orient the axis of the rod 100 closer to the axis of rotation of the pelvis. To facilitate burying the screw into the bone, the screw 105 preferably includes a set screw 107 projecting from the top of the screw head. The screw head also preferably includes a hex driving feature to receive a driving tool from the top. The screw 105 is then threaded into the sacrum from directly above and immediately adjacent the iliac crest. Once the screw is driven deep into the bone, a channel is carved from the sacrum aligned with the oblique canal 106 in the screw 105. This channel will receive the spinal rod 100 when it is loaded into the sacral screw 105. One screw that is well suited for use in this manner is a sacral screw provided by SOFAMOR, SA of Rang du Fliers, France, under part reference, number 9 60 25.

A third feature of the intrasacral fixation resides in a "buttressing" effect provided by the ilium in the region of fixation. In particular, as shown in FIG. 20B, the ilium I overlaps a portion of the sacrum in which the rod 100 is mounted. Thus, the ilium I helps support the distal rod and protect the screw 100 in S1 from excessive stresses that lead to screw pullout in prior systems. Moreover, the insertion of the end portion 102 of the rod 100 into the sacrum adds further resistance to moments and stresses generated by corrective forces applied to the rod 100 and vertebrae.

Moments and stresses are applied to the intrasacral fixation by the in situ contouring of the rod 100 when its distal end 102 is engaged in the sacrum. For example, in FIG. 20B rod benders 109 are shown applied to contour the rod at the lumbosacral junction. Correction at this level may be necessary to address a severe scoliosis or correct an improper pelvic tilt. The sacral "buttress" effect provided by the ilium and the sacral engagement of the rod portion 102 resist the flexural bending loads exerted while the rod is contoured. These same features are beneficial once the instrumentation is complete to enlist the leverage provided by the pelvis in reducing stresses to the sacral screws 105 during the fixation. One further advantage is that the sacral screw 105 can be placed in the S1 vertebra farther from the instrumentation in L5 (not shown), augmented by the rod end portion 102 and the iliac "buttress".

Figure 21A:
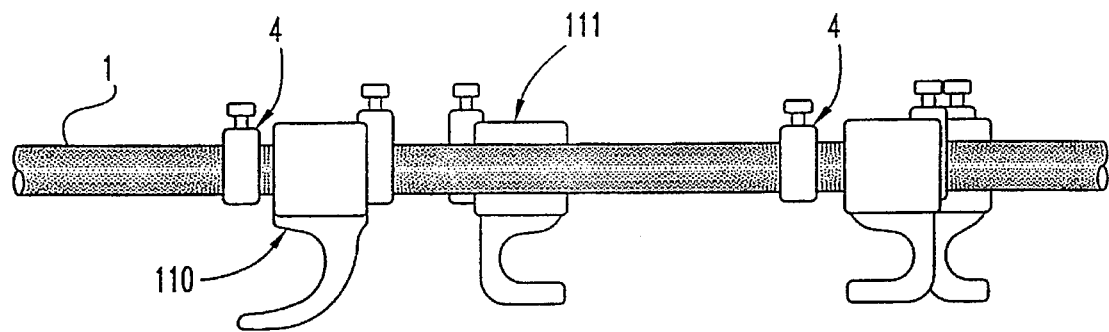
FIGS. 21A–B are side and top elevational views of spinal instrumentation using the multiple lateral connection elements to permit multiple single level instrumentation of a vertebra.
Figure 21B:
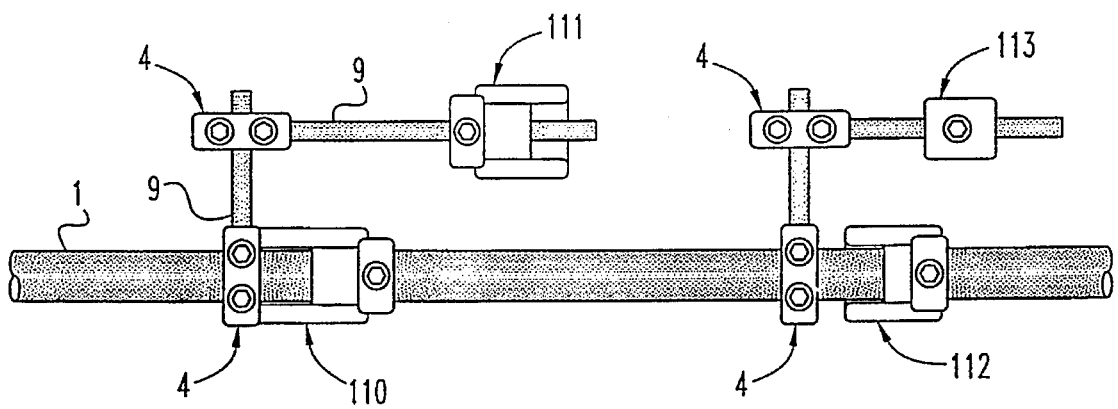

A further application of the lateral connection element 4 described above is depicted in FIGS. 21A–21B. In particular, the lateral connection element 4 provides means for engaging two vertebral fixation elements at the same level. In prior systems, vertebral fixation elements, such as hooks or screws, were mounted serially on the spinal rod. However, this serial approach is limited by the portions of the vertebra available for engaging a hook or screw. Other prior systems provide a lateral extension for supporting a second hook or screw in the same vertebra, but this second screw is necessarily superior or inferior to the first vertebral fixation element.

The present invention provides means for engaging more than one fixation element into a given vertebra. For example, as shown in the left construct in FIGS. 21A–B, a hook 110 is shown mounted to the rod 1 in a manner as depicted in FIG. 1. Immediately adjacent hook 110 is a lateral connection element 4 of the type shown in FIG. 1. A second lateral connection element 4' is engaged to the arm 9 of the first such element 4. The arm 9' of this second element 4' extends parallel with the rod 1 and back toward the level of the hook 110. A second vertebral fixation element, such as hook 111, is then mounted to the second arm 9'.

Alternatively, a construct as shown in the right side of the figures can be implemented using similar lateral connection elements 4. In this configuration, the first hook 112 and second hook 113 are a nearly the same level. In either case, the set of hooks can be manipulated to engage the same vertebra, or can engage adjacent vertebra for distraction.

Moreover, one of the hooks of the pair can be replaced by a bone screw. For example, the hook 112 in the right construct can be replaced by a bone screw, such as the screw assembly 15 in FIG. 3. The screw can be engaged in the pedicle and the hook 113 engaged to the lamina of the same vertebra. The addition of the hook helps strengthen the constrict against pullout of the pedicle screw. Again, it is the versatility of the lateral connection element 4 that perslits fixation constructs not yet found in the art.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A spinal osteosynthesis device comprising:
   at least one rod (1);
   at least two bone anchorage elements (3, 15) configured to be anchored to a vertebra; and
   at least one connection element (4) for connecting the rod (1) to at least one said bone anchorage elements, said connection element including
   a ring (8) which is so dimensioned that the rod can be mounted therein to move freely in rotation and translation;
   means (14) for fixing the ring on said rod; and
   an elongated cylindrical arm (9) radially extending from said ring for connection to said at least one bone anchorage element, said arm and said ring constituting a unit in one piece;

wherein said at least one bone anchorage element (3) includes a U-shaped body (5) defining a passage (10) adapted to receive said cylindrical arm (9) extended therethrough permitting rotation and translation of said U-shaped body about said arm.

2. The spinal osteosynthesis device according to claim 1, wherein said means for fixing includes at least one screw (14) extending through a radial aperture (13) in the ring (8) and bearing against the rod (1).

3. The spinal osteosynthesis device according to claim 1, wherein the ring (8) is open and defines a slot (20) therethrough to said passage (10).

4. The spinal osteosynthesis device according to claim 1, wherein the surface of the arm (9) has a rough finish (11).

5. The device according to claim 4, wherein said rough finish is obtained by knurling.

6. The spinal osteosynthesis device according to claim 1, wherein said ring (8) is provided with a series of apertures (13) arranged on its periphery in such manner that at least one thereof is accessible to the surgeon for inserting a clamping screw (14) therein, regardless of the angular position of the ring on the rod.

7. The spinal osteosynthesis device according to claim 1, wherein said passage (10) of the U-shaped body (5) of the anchorage element is closed by a screw threaded plug fixed to the anchorage element (3) after insertion of the elongated arm (9) of the connection element (4) into said passage, on which the plug acts radially for exerting a clamping force.

8. A spinal fixation system for correction of spinal deformities, comprising:

a longitudinal member sized to extend between a plurality of vertebrae along the length of the spinal column;

a plurality of bone anchorage elements, each having a portion configured for engaging a corresponding one of the plurality of vertebrae, and each having a portion defining a passage therethrough;

a lateral connection element disposed between at least one of said bone anchorage elements and said longitudinal member, said connection element including a body having means for slidably engaging said body to said longitudinal member so that said body is free to move in rotation about and translation along the length of said longitudinal member without being disengaged therefrom; and an elongated arm attached to said body and extending outward therefrom away from said longitudinal member when said body is engaged thereon, said arm configured to be received within said passage of said at least one bone anchorage element so that said at least one bone anchorage element is permitted to move freely in rotation and translation about said elongated arm; and means associated with each of said plurality of bone anchorage elements for fixing said element on one of said longitudinal member or said arm of said lateral connection element.

9. The spinal fixation system of claim 8, wherein:

said longitudinal member is an elongated rod; and said body of said lateral connection element defines an opening therein sized to slidably receive said elongated rod therethrough.

10. The spinal fixation system of claim 9, wherein said body of said lateral connection element is a cylindrical ring encircling said rod.

11. The spinal fixation system of claim 8, wherein:

said at least one bone anchorage element includes a U-shaped body defining said passage for receiving said arm of said lateral connection element therein; and said means for fixing associated with said at least one bone anchorage element includes a fixing element insertable in said U-shaped body of said anchorage element and having a opening therein for receiving said arm therethrough when said fixing element is inserted in said U-shaped body.

12. The spinal fixation system of claim 8, wherein said elongated arm and said body constitute a unit in one piece.

13. The spinal fixation system of claim 8, wherein:

said means for slidably engaging includes an opening sized to slidably receive said longitudinal member therethrough; and said means for fixing includes a screw extending through an aperture in said body intersecting said opening, said screw bearing against said longitudinal member or said arm received within said opening in said body.

14. The spinal fixation system of claim 8, wherein said elongated rod is cylindrical and said opening in said body of said lateral connection element is circular.

15. A method for correction of a spinal deformity comprising the steps of:

implanting a longitudinal member extending between a plurality of vertebrae along a portion of the length of the deformed spine of the patient;

engaging at least one bone anchorage element to each of the plurality of vertebrae;

connecting each bone anchorage element to the longitudinal member; and manually bending the longitudinal member within the patient with the vertebrae connected thereto to thereby manipulate the vertebrae to correct the spinal deformity by the bending of the rod.

16. The method for correction of a spinal deformity of claim 15, wherein said step of connecting each bone anchorage element includes laterally offsetting at least one anchorage element from the longitudinal member.

17. The method for correction of a spinal deformity of claim 16, wherein said step of connecting includes:

connecting a connection element to the longitudinal member to permit relative rotation and translation between the connection element and the longitudinal member; and connecting said at least one anchorage element to said connection element laterally offset from said longitudinal member.

18. The method for correction of a spinal deformity of claim 15 wherein said step of connecting each bone anchorage element includes connecting each element to permit relative rotation and translation between the element and the longitudinal member while maintaining the connection therebetween.

19. The method for correction of a spinal deformity of claim 18, further comprising:

maintaining the connection between each element and the longitudinal member during said bending step while permitting relative rotation and translation; and thereafter fixing each element to the longitudinal member after correction of the spinal deformity.

20. The method for correction of a spinal deformity of claim 19, wherein said step of connecting includes:

connecting a connection element to the longitudinal member to permit relative rotation and translation between the connection element and the longitudinal member; and connecting said at least one anchorage element to said connection element laterally offset from said longitudinal member.

21. The method for correction of a spinal deformity of claim 15 wherein the longitudinal member is a strong ductile rod.

22. The method for correction of a spinal deformity of claim 15, wherein the longitudinal member is an elongated cylindrical rod.

23. The method for correction of a spinal deformity of claim 15, further comprising:

maintaining the connection between each element and the longitudinal member during said bending step, while permitting relative rotation and translation between some of the elements and the longitudinal member; and thereafter fixing each element to the longitudinal member.

24. The method for correction of a spinal deformity of claim 15, further comprising:

fixing some of the bone anchorage elements relative to the longitudinal member prior to said bending step.

25. A method for correction of a spinal deformity comprising the steps of:

implanting an elongated rod extending between a plurality of vertebrae along a portion of the length of the deformed spine of the patient;

engaging a bone anchorage element to each of the plurality of vertebrae;

connecting an elongated connection element to the rod to permit rotation of the connection element relative to the rod;

connecting one of the bone anchorage elements to the elongated connection element to permit translation of the anchorage element relative to the connection element;

connecting the remainder of the bone anchorage elements to the elongated rod;

holding the rod against rotation;

rotating the connection element relative to the rod while permitting the one bone anchorage element to slide along the connection element, to thereby manipulate the vertebra by the rotation of the connection element to which the one bone anchorage element is engaged; and fixing all of the bone anchorage elements relative to the rod.

26. A spinal fixation system for correction of spinal deformities, comprising:

an elongated member sized to extend between a plurality of vertebrae along a portion of the length of the spinal column;

a first bone anchorage element having a body portion with means for mounting said body portion on said elongated rod, and a portion configured to engage one of the plurality of vertebrae;

first and second connection elements, each having a body defining an opening therethrough and an arm integral with said body and extending outward therefrom; and a second bone anchorage element having a second body portion with means for mounting said second body portion on said arm of said second connection element, and a second portion configured to engage said one of the plurality of vertebrae;

wherein said first connection element is engaged to said elongated member with said member extending through said opening in said body of said first connection element, and said second connection element is engaged to said first connection element with said arm of said first connection element extending through said opening in said body of said second connection element.

* * * * *